(12) United States Patent
Matsubara et al.

(10) Patent No.: US 11,712,451 B2
(45) Date of Patent: Aug. 1, 2023

(54) AGENT FOR PROMOTING WOUND HEALING COMPRISING PLATELET-LIKE CELL CO-EXPRESSING PLATELET SURFACE ANTIGEN AND MESENCHYMAL CELL SURFACE ANTIGEN

(71) Applicant: KEIO UNIVERSITY, Tokyo (JP)

(72) Inventors: Yumiko Matsubara, Tokyo (JP); Yasuo Ikeda, Tokyo (JP); Keiichi Tozawa, Tokyo (JP); Yukako Uruga, Tokyo (JP); Masaki Yazawa, Tokyo (JP); Taisuke Mori, Tokyo (JP); Kazuo Kishi, Tokyo (JP)

(73) Assignee: KEIO University, Tokyo (JP)

( * ) Notice: Subject to any disclaimer, the term of this patent is extended or adjusted under 35 U.S.C. 154(b) by 960 days.

(21) Appl. No.: 16/162,546

(22) Filed: Oct. 17, 2018

(65) Prior Publication Data

US 2019/0269732 A1    Sep. 5, 2019

(30) Foreign Application Priority Data

Aug. 21, 2017    (JP) ................................. 2017-158702

(51) Int. Cl.
  *A61K 35/19*    (2015.01)
  *A61P 17/02*    (2006.01)
(52) U.S. Cl.
  CPC .............. *A61K 35/19* (2013.01); *A61P 17/02* (2018.01)
(58) Field of Classification Search
  None
  See application file for complete search history.

(56) References Cited

U.S. PATENT DOCUMENTS

2016/0177265 A1 *  6/2016  Matsubara ........... C12N 5/0644
                                                         435/377

FOREIGN PATENT DOCUMENTS

| JP | 2008-546397 A | 12/2008 |
| JP | 2012-510279 A | 5/2012 |
| JP | 2006-230316 A | 9/2016 |
| WO | WO2006/136244 A2 | 12/2006 |
| WO | WO2010/063743 A1 | 6/2010 |

OTHER PUBLICATIONS

Ehrenfest et al.; Muscles, Ligaments and Tendons Journal 2014; 4 (1): 3-9 (Year: 2014).*

* cited by examiner

*Primary Examiner* — James D Schultz
(74) *Attorney, Agent, or Firm* — Occhiuti & Rohlicek LLP

(57) ABSTRACT

An object of the present invention is to provide, for example, a more practical wound healing accelerator that more effectively accelerates wound healing. More specifically, a feature of the present invention is to provide, for example, a more practical wound healing accelerator that is easily obtained in a larger amount than that of peripheral blood platelet and has a better wound healing effect than that of peripheral blood platelet. The present invention employs a platelet-like cell population coexpressing one or more platelet surface markers and one or more mesenchymal cell surface markers. A wound healing accelerator containing the platelet-like cell population is a more practical wound healing accelerator that more effectively accelerates wound healing. The platelet-like cell population is easily obtained in a larger amount than that of peripheral blood platelet and has a better wound healing effect than that of peripheral blood platelet.

14 Claims, 3 Drawing Sheets

[Figure 1]
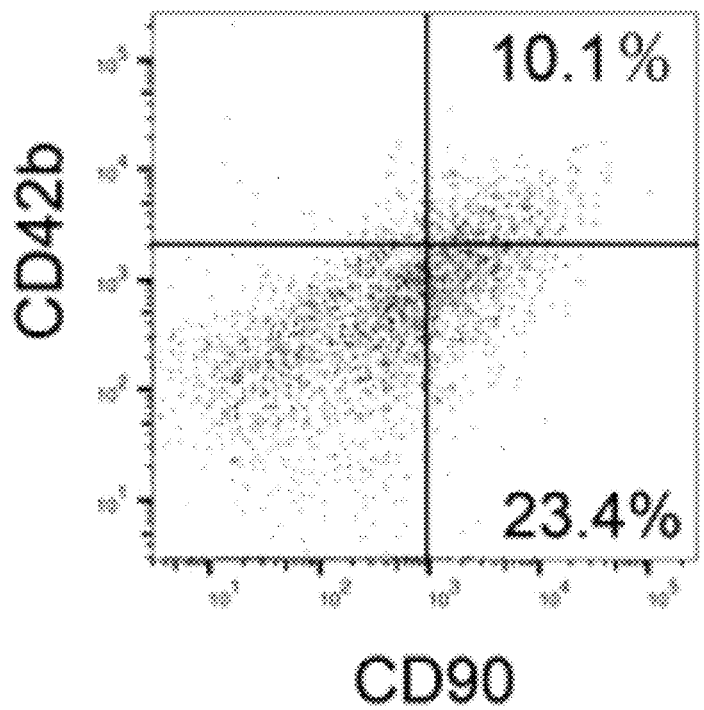
[Figure 2]
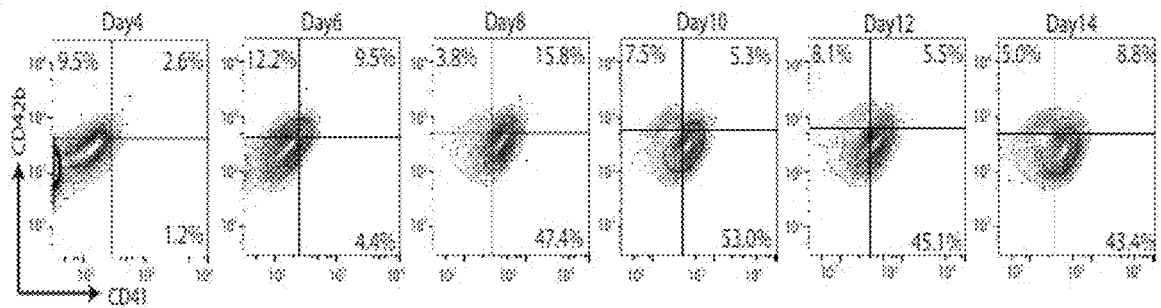
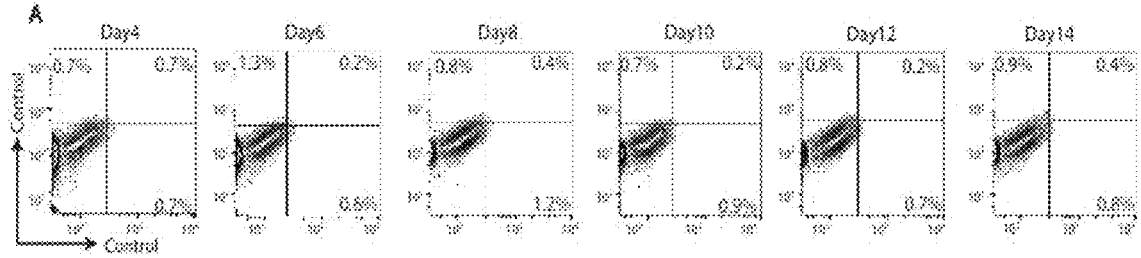

[Figure 3]
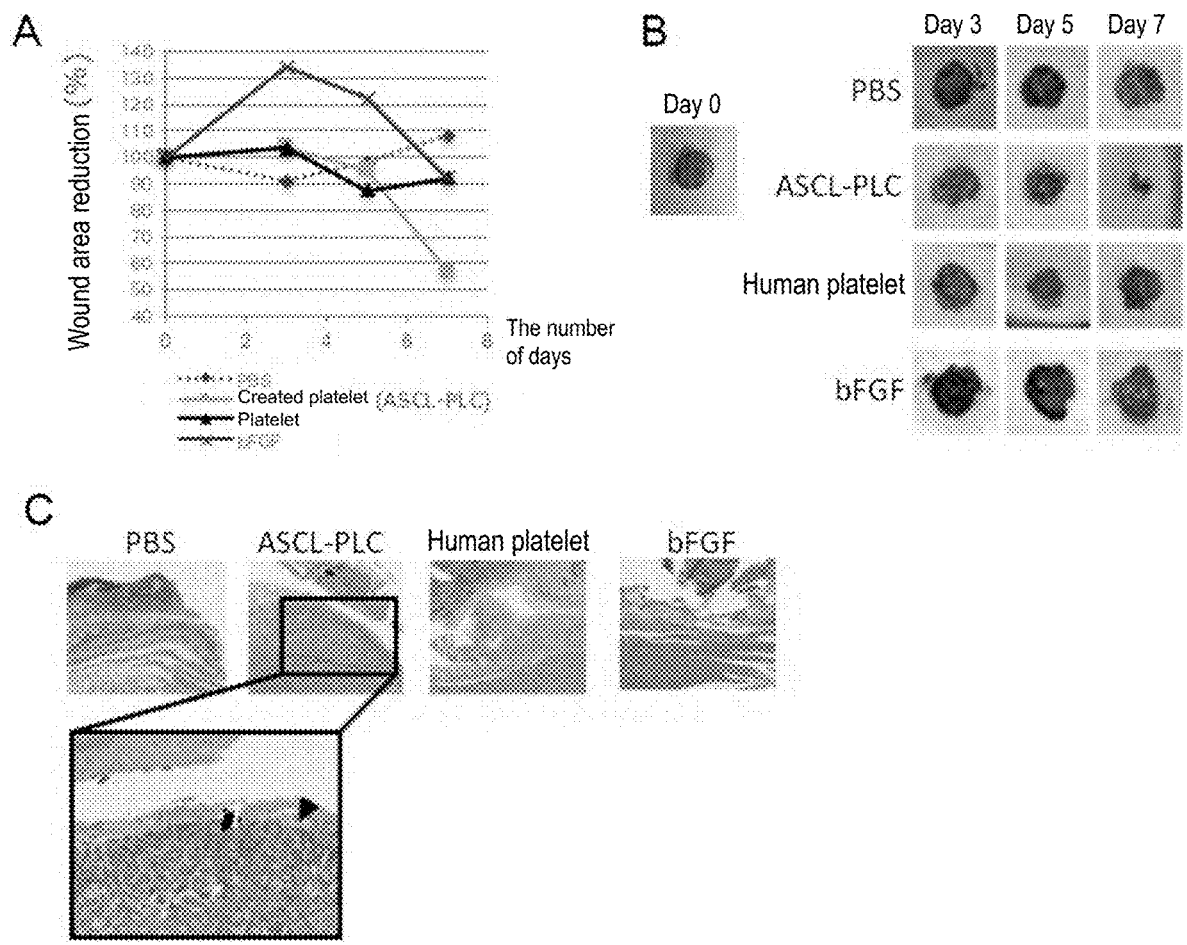

[Figure 4]
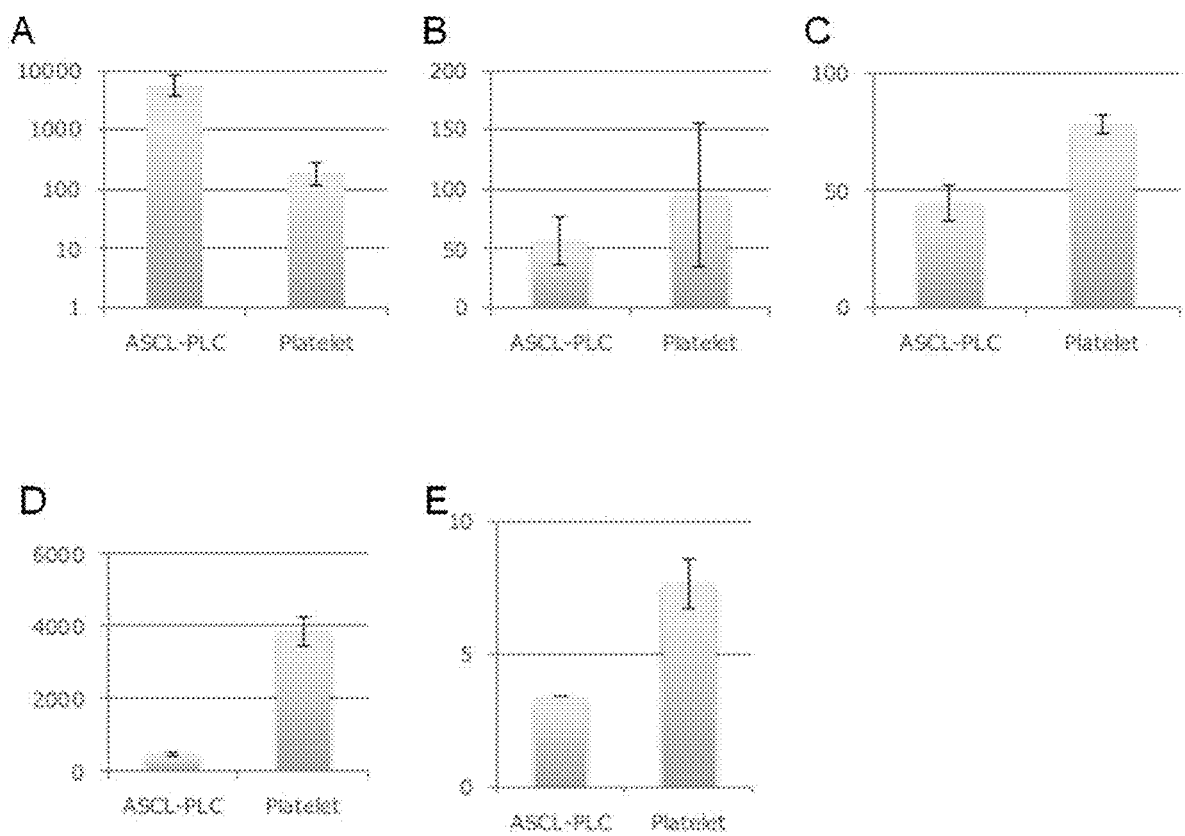

AGENT FOR PROMOTING WOUND HEALING COMPRISING PLATELET-LIKE CELL CO-EXPRESSING PLATELET SURFACE ANTIGEN AND MESENCHYMAL CELL SURFACE ANTIGEN

CROSS-REFERENCE TO RELATED APPLICATIONS

This application claims the priority of Japanese Application No. 2017-158702, filed on Aug. 21, 2017. The content of the application is hereby incorporated by reference in their entirety.

TECHNICAL FIELD

The present invention relates to, for example, a wound healing accelerator comprising platelet-like cells coexpressing a platelet surface antigen and a mesenchymal cell surface antigen.

BACKGROUND ART

Wounds are formed by various causes such as trauma, burn injury, and poor blood circulation. The healing process of the wound is generally classified into four stages: a blood coagulation phase, an inflammation phase, a proliferation phase, and a maturation phase. At the blood coagulation phase, blood coagulated by coagulation factors and platelet forms clots and transiently closes the wound so that growth factors or cytokines, such as platelet-derived growth factor (PDGF), transforming growth factor-β (TGF-β), and vascular endothelial cell growth factor (VEGF), are released from the platelet.

The inflammation phase generally refers to the period when inflammatory response is seen for 3 to 5 days from immediately after injury. The inflammation phase is the phase at which preparations for wound healing are made, and various factors that interfere with wound healing are removed by inflammatory cells such as neutrophils or macrophages. First, neutrophils migrate and release granules containing proteolytic enzymes. The proteolytic enzymes digest and degrade bacteria or foreign matter attached to the wound, and damaged tissues, etc. The neutrophils usually infiltrate into the wound from several minutes after the injury and withdraw within 3 days. Macrophages appear from 2 days after the injury somewhat overlapping with the time of appearance of the neutrophils. The macrophages phagocytize bacteria, foreign matter and necrotic tissues while producing growth factors or cytokines and promoting the growth of vascular endothelial cells, fibroblasts and epidermal cells.

The proliferation phase generally refers to a period of 2 to 3 weeks following the inflammation phase. The proliferation phase is the phase at which granulation tissues are formed, and then, epithelization proceeds. The granulation tissues are constituted by new blood vessels, fibroblasts, macrophages, collagen fiber and stromal cells, etc. Fibroblasts that have migrated into the wound are activated by the growth factors or the cytokines produced by the macrophages and the like to synthesize and extracellularly secrete collagen precursors. The extracellularly secreted collagen precursors are cleaved into collagen molecules by particular peptidase. Thereafter, intramolecular cross-link is formed within the collagen molecules, resulting in collagen fiber.

The maturation phase generally refers to a period subsequent to a lapse of 2 weeks after the injury. The maturation phase corresponds to the final stage of wound healing. The maturation phase is the phase at which the contraction of the wound occurs, and extracellular matrix is reorganized. The collagen fibril that has formed proud flesh is converted to thick bundles of collagen fibril in scar after progression of polymerization. The vascularity of new blood vessels formed within the proud flesh decreases gradually due to the apoptosis of the vascular endothelial cells. As tissue reconstruction proceeds within the dermis, the wound is flattened.

A spray formulation (general name "Trafermin") containing basic fibroblasts (bFGF) as an active ingredient is commercially supplied as a therapeutic agent for pressure ulcer or skin ulcer (burn ulcer and leg ulcer). The bFGF formulation is also used for accelerating the healing of wounds such as trauma, in addition to the treatment of pressure ulcer or skin ulcer. However, as the healing process of the wound is divided into the early stage (inflammation phase), the middle stage (proliferation phase), and the late stage (maturation phase), bFGF acts mainly at the proliferation phase (middle stage) and is low effective at the inflammation phase (early stage). Thus, the bFGF formulation has a low wound healing accelerating effect.

Another method for accelerating wound healing is a therapy which involves the topical application, infusion or the like of autologous platelet obtained from the own peripheral blood of a patient having a wound, to the wound portion (e.g., autologous platelet-rich plasma therapy). This peripheral blood platelet acts from the early stage (inflammation phase) and the middle stage (proliferation phase) and therefore has a high wound healing accelerating effect as compared with the bFGF formulation. However, leukocytes often find their way into peripheral blood platelet during preparation from peripheral blood. In addition, a method optimal for preparing peripheral blood platelet from peripheral blood somewhat differs from person to person. Thus, the preparation method cannot be standardized. For such reasons, it is difficult to prepare a formulation that can be commonly used for many patients. Hence, in Japan, the application of peripheral blood platelet to wounds is not common as standard treatment that is covered by public medical insurance, and the application of autologous platelet prepared from patient's own peripheral blood to the wound of the patient is merely performed by private practice that is not covered by public medical insurance. Furthermore, the autologous platelet liquid for use in the treatment is obtained in only approximately 1 mL from 20 mL of blood, and there is also a limitation on the amount of blood collected. Therefore, the therapy using autologous platelet cannot be applied to a wide range of wounds.

As mentioned above, all of the methods currently used in the treatment of wounds have major problems. Thus, any practical formulation or method that effectively accelerates wound healing has not yet been developed under these circumstances.

Accordingly, attempts have heretofore been made to develop alternative methods for accelerating wound healing. For example, patent document 1 states that when mesenchymal stem cells obtained by subculturing several times cells adhering to a plastic dish among mesenchymal stem cells obtained from bone marrow, menstrual blood or cord blood were transplanted to an incisional wound, the healing of the wound was accelerated, and scar formation was suppressed. However, the bone marrow, the menstrual blood, or the cord blood is not easy to obtain, and the amount thereof is also small. For such reasons, the practicality of this technique is not sufficient. Patent document 2 describes a method for preparing adipose-derived stem cells, comprising exposing adipose-derived stem cells to a CD26 antagonist or inhibitor. Patent document 2 states that the adipose-derived stem cells may be used for preventing, treating or ameliorating one or more symptoms associated with wound treatment and diseases such as tissue damage, allergic response, immune disease, autoimmune disease, immune-mediated disease, inflammatory disease, and chronic inflammatory disease. Nonetheless, pharmacological data supporting this is not fully described therein, and it is uncertain whether the desired effect is actually exerted. Patent document 3 describes a method for treating fistula or wound, comprising closing the fistula or the wound with a suture, and delivering particular adipose tissue-derived stromal stem cells to the sutured fistula or wound.

Thus, the cells used in patent documents 1 to 3 are nucleated cells and differ cytologically from the platelet-like cells according to the present invention. There has been a demand for a more practical formulation or method that more effectively accelerates wound healing.

PRIOR ART DOCUMENTS

Patent Documents

Patent document 1: Japanese unexamined Patent Application Publication No. 2006-230316
Patent document 2: Japanese unexamined Patent Application Publication (Translation of PCT Application) No. 2012-510279
Patent document 3: Japanese unexamined Patent Application Publication (Translation of PCT Application) No. 2008-546397

SUMMARY OF THE INVENTION

Object to be Solved by the Invention

As also described in the section of Background Art, all of the methods currently used in the treatment of wounds have major problems. Thus, any practical formulation or method that effectively accelerates wound healing has not yet been developed under these circumstances. For example, a spray formulation (general name "Trafermin") containing basic fibroblasts (bFGF) as an active ingredient is commercially supplied as a therapeutic agent for pressure ulcer or skin ulcer (burn ulcer and leg ulcer). The bFGF formulation is also used for accelerating the healing of wounds such as trauma, in addition to the treatment of pressure ulcer or skin ulcer. However, as the healing process of the wound is divided into the early stage (inflammation phase), the middle stage (proliferation phase), and the late stage (maturation phase), bFGF acts mainly at the proliferation phase (middle stage) and is low effective at the inflammation phase (early stage). Thus, the bFGF formulation has a low wound healing accelerating effect. Another method for accelerating wound healing is a therapy which involves the topical application, infusion or the like of autologous platelet obtained from the own peripheral blood of a patient having a wound, to the wound portion (e.g., autologous platelet-rich plasma therapy). This peripheral blood platelet acts from the early stage (inflammation phase) and the middle stage (proliferation phase) and therefore has a high wound healing accelerating effect as compared with the bFGF formulation. However, leukocytes often find their way into peripheral blood platelet during preparation from peripheral blood. In addition, a method optimal for preparing peripheral blood platelet from peripheral blood somewhat differs from person to person. Thus, the preparation method cannot be standardized. For such reasons, it is difficult to prepare a formulation that can be commonly used for many patients. Hence, in Japan, the application of peripheral blood platelet to wounds is not common as standard treatment that is covered by public medical insurance, and the application of autologous platelet prepared from patient's own peripheral blood to the wound of the patient is merely performed by private practice that is not covered by public medical insurance. Furthermore, the autologous platelet liquid for use in the treatment is obtained in only approximately 1 mL from 20 mL of blood, and there is also a limitation on the amount of blood collected. Therefore, the therapy using autologous platelet cannot be applied to a wide range of wounds.

An object of the present invention is to provide, for example, a more practical wound healing accelerator that more effectively accelerates wound healing. More specifically, an object of the present invention is to provide, for example, a more practical wound healing accelerator that is easily obtained in a larger amount than that of peripheral blood platelet and has a better wound healing effect than that of peripheral blood platelet.

Means to Solve the Object

The present inventors have previously studied on treatment utilizing mesenchymal cells such as preadipocytes. The present inventors developed, for example, a method for conveniently manufacturing ex vivo megakaryocytes or platelet in a large amount at a lower cost or more efficiently in a relatively short period by culturing mesenchymal cells such as preadipocytes in a basal medium for mesenchymal cell culture containing an iron ion and an iron transporter, and filed a patent application (International Publication No. WO 2014/208100). The medium is a medium containing an iron ion and an iron transporter in a basal medium for mesenchymal cell culture and is a medium for induction of differentiation into megakaryocytic cells (megakaryocytes and/or platelet). The present inventors also developed a method for manufacturing a vertebrate adipose tissue-derived mesenchymal cell line, comprising: a step (A) of inducing the differentiation of one or more cells selected from a stromal vascular fraction including a mesenchymal stem cell, a preadipocyte and a stromal cell of a vertebrate adipose tissue into a mature adipocyte; and a step (B) of inducing the dedifferentiation of the mature adipocyte obtained in the step (A) to obtain a vertebrate adipose tissue-derived mesenchymal cell line, and filed a patent application (Japanese Patent Application No. 2015-234836). The present inventors further developed a method for manufacturing a mesenchymal cell having the promoted expression of a c-MPL receptor on the cell surface, comprising: step A of culturing a mesenchymal cell in a basal culture medium for mesenchymal cell culture containing a c-MPL receptor agonist; and step B of obtaining the mesenchymal cell having the promoted expression of a c-MPL receptor on the cell surface, and filed a patent application (PCT/JP2016/003626).

While pursuing diligent studies to attain the object of providing, for example, a more practical wound healing accelerator that more effectively accelerates wound healing, the present inventors have created a mesenchymal cell line from a subcutaneous adipose tissue and attempted analysis on the characteristics of a platelet-like cell population obtained by culturing the mesenchymal cell line in a medium modified from a medium for induction of differentiation into megakaryocytic cells (hereinafter, also referred to as a "modified medium for induction of differentiation into megakaryocytic cells"), and analysis on the physiological function thereof. As a result of analyzing a surface antigen marker of the platelet-like cell population, the present inventors have found for the first time that not only a platelet marker but a mesenchymal cell marker is coexpressed in the platelet-like cell population. The present inventors have further evaluated the wound healing accelerating effect of the platelet-like cell population through the use of a complete loss created in the mouse skin and consequently found for the first time that the platelet-like cell population exerts a remarkably excellent wound healing accelerating effect as compared with peripheral blood platelet or a bFGF formulation. The present inventors have completed the present invention on the basis of these findings.

Specifically, the present invention relates to:
(1) a wound healing accelerator comprising a platelet-like cell population coexpressing one or more platelet surface markers and one or more mesenchymal cell surface markers,
(2) the wound healing accelerator according to (1) described above, wherein the wound healing accelerator is topically administered to a wound,
(3) the wound healing accelerator according to (1) or (2) described above, wherein in the platelet-like cell population, the proportion of CD29-positive cells is 60% or more, the proportion of CD42b-positive cells is 5% or more, and the proportion of CD90-positive cells is 30% or more,
(4) the wound healing accelerator according to any one of (1) to (3) described above, wherein the platelet-like cell population further satisfies one or more (preferably an optional combination of 3 or more, 4 or more, 5 or more, 6 or more, 7 or more, 8 or more, 9 or more, 10 or more, 11 or more, 12 or more, 13 or more, 14 or more, 15 or more, 16 or more or 17) of the following conditions:
the proportion of CD9-positive cells is 30% or less;
the proportion of CD13-positive cells is 30% or more;
the proportion of CD26-positive cells is 15% or more;
the proportion of CD36-positive cells is 40% or less;
the proportion of CD41/61-positive cells is 60% or less;
the proportion of CD42b-positive cells is 5% or more;
the proportion of CD41-positive cells is 20% or more;
the proportion of CD44-positive cells is 30% or more;
the proportion of CD49b-positive cells is 30% or more;
the proportion of CD61-positive cells is 30% or less;
the proportion of CD63-positive cells is 60% or more;
the proportion of CD73-positive cells is 40% or more;
the proportion of CD95-positive cells is 20% or more;
the proportion of CD107a-positive cells is 45% or more;
the proportion of CD107b-positive cells is 20% or more;
the proportion of CD147-positive cells is 50% or less; and
the proportion of CD164-positive cells is 15% or more,
(5) the wound healing accelerator according to any one of (1) to (4) described above, wherein the platelet-like cell population is a human-derived platelet-like cell population,
(6) the wound healing accelerator according to any one of (1) to (5) described above, wherein the platelet-like cell population is a platelet-like cell population in which an amount of a basic fibroblast growth factor produced by the platelet-like cell population is 10 or more times an amount of the basic fibroblast growth factor produced by a cell population of platelet, the amount being measured by the following measurement method:

(Method for Measuring Amount of Basic Fibroblast Growth Factor Produced)
suspending cells of the cell population at $20 \times 10^8$ cells/mL in 20 µL of phosphate-buffered saline and stimulated with 10 mM $CaCl_2$ for 15 minutes, and then measuring the amount of the basic fibroblast growth factor in the phosphate-buffered saline,
(7) the wound healing accelerator according to any one of (1) to (6) described above, wherein a ratio of an open wound area of the platelet-like cell population is 90% or less, the open wound area being measured by the following measurement method:
(Method for Measuring Open Wound Area)
ratio of an open wound area after a lapse of 7 to 9 days from the start of application of the wound healing accelerator to a wound [area ratio calculated according to (open wound area (%) of each administration group/open wound area (%) of a control administration group)×100], and
(8) the wound healing accelerator according to any one of (1) to (7) described above, wherein the wound is one or more wounds selected from the group consisting of incised wound, lacerated wound, chop wound, puncture wound, impalement wound, contused wound, dermabrasion, bite wound, gunshot wound, pressure ulcer, cut, rupture, sting, bruising, bite, abrasion, burn, skin ulcer, decubitus, erosion, surgical wound and anastomotic leakage.

The present invention also relates to:
(9) the wound healing accelerator according to any one of (1) to (5) described above, wherein the platelet-like cell population is manufactured by a method comprising the steps of:
(A) inducing a differentiation of one or more cells selected from a stromal vascular fraction including a mesenchymal stem cell, a preadipocyte and a stromal cell of a vertebrate adipose tissue into a mature adipocyte;
(B) inducing a dedifferentiation of the mature adipocyte obtained in the step (A) to obtain a vertebrate adipose tissue-derived mesenchymal cell line; and
(C) culturing a adipose tissue-derived mesenchymal cell line obtained in the step (B) in a modified medium for induction of differentiation into megakaryocytic cells containing an iron ion and an iron transporter, and collecting a platelet-like cell population from the culture product, wherein
the modified medium for induction of differentiation into megakaryocytic cells in the step (C) is free from bovine serum albumin, LDL cholesterol, deoxyribonucleotide triphosphate, and 2-mercaptoethanol and contains human serum albumin, iron-bound transferrin, insulin, and monothioglycerol,
(10) the wound healing accelerator according to (9) described above, wherein after obtaining the adipose tissue-derived mesenchymal cell line in the step (B) and before culturing the cell line in the modified medium for induction of differentiation into megakaryocytic cells containing an iron ion and an iron transporter in the step (C), a selection of a cell by using the presence or absence of an expression of a particular cell surface marker as an index is not performed for the cell line, and
(11) the wound healing accelerator according to (9) or (10) described above, wherein in the step (C), the method for collecting the platelet-like cell population from the culture product does not comprise a selection of a cell by using the presence or absence of the expression of a particular cell surface marker as an index.

Effect of the Invention

The present invention can provide, for example, a more practical wound healing accelerator that more effectively accelerates wound healing. More specifically, the present invention can provide, for example, a more practical wound healing accelerator that is easily obtained in a larger amount than that of peripheral blood platelet and has a better wound healing effect than that of peripheral blood platelet.

BRIEF DESCRIPTION OF DRAWINGS

FIG. 1 shows results of culturing a subcutaneous adipose-derived mesenchymal cell line in a modified medium for induction of differentiation into megakaryocytic cells, and analyzing the expression of cell surface markers (platelet surface antigen CD42b and mesenchymal stem cell surface antigen CD90) in the obtained platelet-like cells (ASCL-PLC).

FIG. 2 shows results of analyzing the coexpression of CD41 and CD42b in ASCL-PLC. When the subcutaneous adipose-derived mesenchymal cell line was cultured in the modified medium for induction of differentiation into megakaryocytic cells, cells expressing the platelet surface antigen were observed.

FIG. 3 shows results of analyzing over time the rate of wound area reduction (FIGS. 3A and 3B) and the morphology of a wound site (FIG. 3C) when 4 types of components (PBS, human platelet, ASCL-PLC, or bFGF) were each topically applied to the wound site of a NSG mouse.

FIG. 4 shows results of measuring the amounts of 5 types of cytokines (bFGF [FIG. 4A], PDGF [FIG. 4B], VEGF-A [FIG. 4C], TGF-β [FIG. 4D], and EGF [FIG. 4E]) produced from ASCL-PLC and human platelet by calcium stimulation. The numeric value on the ordinate represents the amount of each cytokine produced (pg/mL).

MODE OF CARRYING OUT THE INVENTION

The present invention includes:
[1] a wound healing accelerator comprising a platelet-like cell population coexpressing one or more platelet surface markers and one or more mesenchymal cell surface markers (hereinafter, also referred to as the "wound healing accelerator of the present invention");
[2] a platelet-like cell population coexpressing one or more platelet surface markers and one or more mesenchymal cell surface markers (hereinafter, also referred to as the "platelet-like cell population of the present invention");
[3] a method for accelerating wound healing, comprising administering a platelet-like cell population coexpressing one or more platelet surface markers and one or more mesenchymal cell surface markers to a patient having a wound (hereinafter, also referred to as the "wound healing acceleration method of the present invention");
[4] use of a platelet-like cell population coexpressing one or more platelet surface markers and one or more mesenchymal cell surface markers in the manufacture of a wound healing accelerator;
[5] a platelet-like cell population coexpressing one or more platelet surface markers and one or more mesenchymal cell surface markers for use in the treatment of a wound;
[6] a platelet-like cell population coexpressing one or more platelet surface markers and one or more mesenchymal cell surface markers for use as a therapeutic agent for a wound; etc.

The wound healing accelerator can also be used as a therapeutic agent for a wound. The method for accelerating wound healing can also be used as a method for treating a wound. The therapeutic agent for a wound is a therapeutic agent for a wound that accelerates wound healing. The method for treating a wound is a wound treatment method that accelerates wound healing. In the present specification, the proportion of a cell surface marker-positive cell in the platelet-like cell population means a proportion measured on 12 days after the start of culture of mesenchymal cells in a modified medium for induction of differentiation into megakaryocytic cells containing an iron ion and an iron transporter, and preferably includes a proportion measured by a method described in Example 3 mentioned later.

(Acceleration of Wound Healing)

In the present specification, the phrase "accelerating wound healing" refers to accelerating a series of mechanisms consisting of the first step of performing hemostasis ascribable to platelet aggregation and vasoconstriction at the location of a wounded surface formed by a wound, and the uptake of killed cells on the wounded surface by macrophages, the second step of performing the repair of the wounded surface by a granulation tissue composed mainly of collagen secreted by fibroblasts, and the third step of converting the granulation tissue to a scar tissue for stabilization, or the mechanism of action of any of the first to third steps. The phrase "having a wound healing accelerating effect" for the platelet-like cell population or the wound healing accelerator of the present invention means that in the case of applying the platelet-like cell population or the wound healing accelerator of the present invention to a wound, the period required to heal the wound is short as compared with the case of not applying the platelet-like cell population or the wound healing accelerator of the present invention thereto.

The presence or absence of the wound healing accelerating effect or the degree thereof, or a therapeutic effect on a wound or the degree thereof can be evaluated on the basis of the rate of decrease in wound area after a lapse of a given period and can be calculated by, for example, the measurement of an open wound diameter. A faster decrease in wound area can be regarded as a higher wound healing accelerating effect or therapeutic effect on a wound. Preferred examples of the degree of the wound healing accelerating effect or the therapeutic effect on a wound according to the present invention include approximately 90% or less, preferably 80% or less, more preferably 70% or less, even more preferably 60% or less, still more preferably 55% or less, further preferably 50% or less in terms of a ratio of an open wound area [area ratio calculated according to (open wound area (%) of each administration group/open wound area (%) of a control administration group)×100] after a lapse of 7 to 9 days from the start of application of the platelet-like cell population or the wound healing accelerator according to the present invention to a wound (e.g., a wound created in Example 5 mentioned later). From such reduction in the ratio of an open wound area, it is confirmed that a favorable wound healing accelerating effect or therapeutic effect on a wound is exerted. The control administration group described above means a group given a substance having the same formulation except that the substance is free from the platelet-like cell population or the wound healing accelerator according to the present invention. In the case of administering, for example, the platelet-like cell population according to the present invention suspended in a PBS solution to an administration group of the wound healing accelerator according to the present invention, a group given a PBS solution can be used as the control administration group.
(Wound)

In the present specification, the "wound" is not particularly limited as long as the wound is a wound whose healing is accelerated by the platelet-like cell population or the wound healing accelerator according to the present invention. Examples thereof include one or more wounds selected from the group consisting of incised wound, lacerated wound, chop wound, puncture wound, impalement wound, contused wound, dermabrasion, bite wound, gunshot wound, pressure ulcer, cut, rupture, sting, bruising, bite, abrasion, burn, skin ulcer, erosion, surgical wound and anastomotic leakage. Among these wounds, a wound caused by surgery is treated by the topical application of platelet-rich plasma to the wound. Therefore, the platelet-like cell population or the wound healing accelerator according to the present invention is considered to exert a wound healing accelerating effect on the wounds listed above. In the present specification, the "wound" may include fistula or may be a wound other than fistula. In the present specification, the "surgical wound" means a wound formed during surgery and is not particularly limited by its type, etc. as long as the surgical wound is such a wound. Preferred examples of the "surgical wound" include one or more wounds selected from the group consisting of incised wound, puncture wound, cut and sting formed during surgery. In the present specification, the "anastomotic leakage" means a wound in which sufficient fusion between tissues does not occur at a site where the wound (preferably a surgical wound) has been sutured (hereinafter, also simply referred to as a "suture site") so that a portion or the whole of the suture site is dissociated, and is not particularly limited by its type, etc. as long as the anastomotic leakage is such a wound. Examples of the "anastomotic leakage" include anastomotic leakage in which when the length of the whole suture site of the wound (preferably a surgical wound) is defined as 100, the proportion of the length of an unfused site at the suture site is preferably 1 to 100, more preferably 20 to 100, even more preferably 50 to 100.

(Platelet-Like Cell Population of Present Invention)

The platelet-like cell population of the present invention is not particularly limited as long as the platelet-like cell population is a platelet-like cell population coexpressing one or more platelet surface markers and one or more mesenchymal cell surface markers. Among others, the platelet-like cell population of the present invention is preferably a mesenchymal cell-derived platelet-like cell population, more preferably a platelet-like cell population obtained by culturing mesenchymal cells in a medium for induction of differentiation into megakaryocytic cells, particularly preferably a platelet-like cell population obtained by culturing preadipocytes, subcutaneous adipose tissue-derived mesenchymal stem cells, or the like (preferably an adipose tissue-derived mesenchymal cell line created by a method described in Example 1 mentioned later) in a modified medium for induction of differentiation into megakaryocytic cells by a method described in Example 2 mentioned later. In the present invention, the "mesenchymal cell-derived" platelet-like cell population is not a cell population obtained by culturing hematopoietic stem cells in a medium for induction of differentiation into megakaryocytic cells, but means a cell population obtained by culturing mesenchymal cells in a medium for induction of differentiation into megakaryocytic cells (preferably a "modified medium for induction of differentiation into megakaryocytic cells"). For the culture of mesenchymal cells in a medium for induction of differentiation into megakaryocytic cells (preferably a "modified medium for induction of differentiation into megakaryocytic cells"), it is also preferred that the mesenchymal cells should not be cocultured with hematopoietic stem cells.

In the present invention, the "platelet-like cell population coexpressing one or more platelet surface markers and one or more mesenchymal cell surface markers" means a platelet-like cell population comprising a platelet-like cell expressing one or more platelet surface markers (platelet-like cell positive to one or more platelet surface markers) and a platelet-like cell expressing one or more mesenchymal cell surface markers (platelet-like cell positive to one or more mesenchymal cell surface markers), and may be a platelet-like cell population comprising the platelet-like cell positive to one or more platelet surface markers and the platelet-like cell positive to one or more mesenchymal cell surface markers, respectively. A platelet-like cell population at least partially comprising a platelet-like cell positive to one or more platelet surface markers and positive to one or more mesenchymal cell surface markers, is preferred. The "platelet-like cell" described above refers to a cell having at least the following features among the features of platelet:

having no nucleus;
having a size of 1 to 10 µm; and
having a wound healing accelerating effect.

In the present invention, the platelet-like cell population comprising the "platelet-like cell expressing one or more platelet surface markers (platelet-like cell positive to one or more platelet surface markers)" is not particularly limited as long as the platelet-like cell population comprises a platelet-like cell expressing at least CD29. Preferred examples thereof include a platelet-like cell population further comprising a platelet-like cell expressing one or more (preferably 3) platelet surface markers selected from the group consisting of CD49b, CD42b and CD41. In the present invention, the "platelet-like cell population comprising a platelet-like cell expressing two or more platelet surface markers" means a platelet-like cell population comprising a platelet-like cell expressing optional one platelet surface marker (platelet-like cell positive to optional one platelet surface marker) among the two or more platelet surface markers, and a platelet-like cell expressing the other optional one or more platelet surface markers (platelet-like cell positive to the other optional one or more platelet surface markers), and may be a platelet-like cell population comprising the platelet-like cell positive to optional one platelet surface marker and the platelet-like cell positive to the other optional one or more platelet surface markers, respectively. A platelet-like cell population at least partially comprising a platelet-like cell positive to optional one platelet surface marker and positive to the other optional one or more platelet surface markers, is preferred.

Specific examples of the platelet-like cell population comprising a platelet-like cell expressing the platelet surface marker CD29 include a platelet-like cell population in which the proportion of CD29-positive cells is preferably 60% or more, more preferably 70 to 90%, even more preferably 75 to 85%. Specific examples of the platelet-like cell population further comprising a platelet-like cell expressing one or more (preferably 3) platelet surface markers selected from the group consisting of CD49b, CD42b and CD41 in addition to CD29 preferably include a platelet-like cell population that satisfies the following numeric range of the proportion of a positive cell as to one or more (preferably 3) platelet surface markers selected from the group consisting of CD49b, CD42b and CD41:

the proportion of CD49b-positive cells is preferably 30% or more (more preferably 30 to 85%, even more preferably 30 to 70%);

the proportion of CD42b-positive cells is preferably 5% or more (more preferably 6 to 80%, even more preferably 7 to 60%, still more preferably 8 to 40%); and the proportion of CD41-positive cells is preferably 20% or more (more preferably 20 to 85%, even more preferably 30 to 70%).

In the present invention, the platelet-like cell population comprising the "platelet-like cell expressing one or more mesenchymal cell surface markers (platelet-like cell positive to one or more mesenchymal cell surface markers)" is not particularly limited as long as the platelet-like cell population comprises a platelet-like cell expressing at least CD90. Preferred examples thereof include a platelet-like cell population further comprising a platelet-like cell expressing one or more (preferably 3 or more, more preferably 5 or more, even more preferably 7 or more, still more preferably 8) mesenchymal cell surface markers selected from the group consisting of CD13, CD26, CD44, CD73, CD77, CD81, CD95 and CD164. In the present invention, the "platelet-like cell population comprising a platelet-like cell expressing two or more mesenchymal cell surface markers" means a platelet-like cell population comprising a platelet-like cell expressing optional one mesenchymal cell surface marker (platelet-like cell positive to optional one mesenchymal cell surface marker) among the two or more mesenchymal cell surface markers, and a platelet-like cell expressing the other optional one or more mesenchymal cell surface markers (platelet-like cell positive to the other optional one or more mesenchymal cell surface markers), and may be a platelet-like cell population comprising the platelet-like cell positive to optional one mesenchymal cell surface marker and the platelet-like cell positive to the other optional one or more mesenchymal cell surface markers, respectively. A platelet-like cell population at least partially comprising a platelet-like cell positive to optional one mesenchymal cell surface marker and positive to the other optional one or more mesenchymal cell surface markers, is preferred.

Specific examples of the platelet-like cell population comprising a platelet-like cell expressing the mesenchymal cell surface marker CD90 include a platelet-like cell population in which the proportion of CD90-positive cells is preferably 30% or more, more preferably to 90%, even more preferably 35 to 70%. Preferred examples thereof include a platelet-like cell population that further satisfies the following numeric range of the proportion of a positive cell as to one or more (preferably 3 or more, more preferably 5 or more, even more preferably 7 or more, still more preferably 8) mesenchymal cell surface markers selected from the group consisting of CD13, CD26, CD44, CD73, CD77, CD81, CD95 and CD164 in addition to CD90:

the proportion of CD13-positive cells is 30% or more (preferably 30 to 80%, more preferably 35 to 65%);

the proportion of CD26-positive cells is 15% or more (preferably 15 to 60%, more preferably 20 to 45%);

the proportion of CD44-positive cells is 30% or more (preferably 30 to 80%, more preferably 35 to 65%);

the proportion of CD73-positive cells is 40% or more (preferably 40 to 95%, more preferably 45 to 80%);

the proportion of CD95-positive cells is 20% or more (preferably 20 to 70%, more preferably 25 to 55%); and the proportion of CD164-positive cells is 15% or more (preferably 15 to 55%, more preferably 20 to 40%).

As mentioned above, preferred examples of the platelet-like cell population of the present invention include a platelet-like cell population at least partially comprising a platelet-like cell positive to one or more platelet surface markers and positive to one or more mesenchymal cell surface markers. Specific examples thereof preferably include a platelet-like cell population that satisfies the following proportion of a positive cell: the proportion of a cell positive to CD42b and positive to CD90 is 3% or more (preferably 3 to 80%, more preferably 5 to 40%, even more preferably 5 to 20%).

In a preferred aspect, examples of the platelet-like cell population of the present invention include a platelet-like cell population in which the expression of one or more particular platelet surface markers (hereinafter, also referred to as "low-expression platelet surface markers") is reduced as compared with its expression in a cell population of usual platelet. The "platelet-like cell population in which the expression of one or more low-expression platelet surface markers is reduced as compared with its expression in a cell population of usual platelet" means a platelet-like cell population in which the proportion of a cell positive to one or more low-expression platelet surface markers is lower than that in the cell population of usual platelet. Examples of the "low-expression platelet surface marker" include one or more (preferably 3 or more, more preferably 5 or more) markers selected from the group consisting of CD9, CD36, CD41/61, CD61 and CD147. The term "CD41/61" means a complex of CD41 and CD61, and the CD41/61-positive cell means a cell expressing the complex of CD41 and CD61.

Specific examples of the platelet-like cell population in which the expression of one or more low-expression platelet surface markers is reduced as compared with its expression in a cell population of usual platelet preferably include a platelet-like cell population that satisfies the following numeric range of the proportion of a positive cell as to one or more (preferably 3 or more, more preferably 5 or more) low-expression platelet surface markers selected from the group consisting of CD9, CD36, CD41/61, CD61 and CD147:

the proportion of CD9-positive cells is 30% or less (preferably 0 to 20%, more preferably 0.5 to 15%);

the proportion of CD36-positive cells is 40% or less (preferably 0 to 30%, more preferably 0.5 to 20%);

the proportion of CD41/61-positive cells is 60% or less (preferably 0 to 40%, more preferably 0.5 to 25%);

the proportion of CD61-positive cells is 30% or less (preferably 0 to 10%, more preferably 0.1 to 8%); and the proportion of CD147-positive cells is 50% or less (preferably 0 to 40%, more preferably 1 to 30%).

In a preferred aspect, examples of the platelet-like cell population of the present invention include a platelet-like cell population comprising a platelet-like cell positive to one or more platelet surface markers and a platelet-like cell positive to one or more mesenchymal cell surface markers and further comprising a platelet-like cell positive to one or more surface markers of activated platelet selected from CD107a and CD107b. The platelet-like cell positive to the activated platelet surface marker may be a cell different from the platelet-like cell positive to one or more platelet surface markers or the platelet-like cell positive to one or more mesenchymal cell surface markers. The platelet-like cell population of the present invention is preferably a platelet-like cell population at least partially comprising a platelet-like cell positive to the activated platelet surface marker and positive to one or more platelet surface markers, or a platelet-like cell positive to the activated platelet surface marker and positive to one or more mesenchymal cell surface markers.

Specific examples of the platelet-like cell population comprising a platelet-like cell positive to one or more activated platelet surface markers selected from CD107a and CD107b preferably include a platelet-like cell population that satisfies the following numeric range of the proportion of a positive cell as to one or more activated platelet surface markers selected from CD107a and CD107b:

the proportion of CD107a-positive cells is 15% or more (more preferably 25 to 80%, even more preferably 45 to 70%); and the proportion of CD107b-positive cells is 10% or more (more preferably 15 to 70%, even more preferably 20 to 55%).

The platelet-like cell population of the present invention may be (a) a platelet-like cell population comprising a selected platelet-like cell having a particular cell surface marker profile (i.e., a platelet-like cell expressing a particular cell surface marker or a particular combination of cell surface markers), or (b) a platelet-like cell population having an improved or reduced proportion of a platelet-like cell having a particular cell surface marker profile, by using the presence or absence of the particular cell surface marker or the particular combination of cell surface markers as an index, or may not be such a platelet-like cell population. In the platelet-like cell population, the proportion of a platelet-like cell expressing a particular cell surface marker or a particular combination of cell surface markers includes each of the proportions of cells positive to particular cell surface markers listed in the present specification, or every combination of the proportions.

In a preferred aspect, examples of the platelet-like cell population of the present invention include a platelet-like cell population in which the amount of a basic fibroblast growth factor (bFGF) produced, measured by the following measurement method is 10 or more times, preferably 30 or more times, more preferably 40 to 80 times, even more preferably 50 to 70 times, the amount of the basic fibroblast growth factor produced by a cell population of platelet:

(Method for Measuring Amount of Basic Fibroblast Growth Factor Produced)

cells of the cell population are suspended at $20 \times 10^8$ cells/mL in 20 μL of phosphate-buffered saline and stimulated with 10 mM $CaCl_2$ for 15 minutes, followed by the measurement of the amount of the basic fibroblast growth factor in the phosphate-buffered saline.

Preferred examples of the formulation of the PBS solution for use in the suspension described above include 8 g/L NaCl, 0.2 g/L KCl, 1.44 g/L $Na_2HPO_4$, and 0.24 g/L $KH_2PO_4$ (pH 7.4).

(Wound Healing Accelerator, Etc. of Present Invention)

The platelet-like cell population of the present invention may be used in itself as the wound healing accelerator, the pharmaceutical composition for wound healing acceleration, the therapeutic agent for a wound or the pharmaceutical composition for wound treatment of the present invention (in the present specification, also referred to as the "wound healing accelerator, etc. of the present invention"). Alternatively, the platelet-like cell population of the present invention may be supplemented with a pharmacologically and pharmaceutically acceptable carrier or the like to prepare the wound healing accelerator, etc. of the present invention. Preferred examples of the pharmacologically and pharmaceutically acceptable carrier include a physiologically acceptable buffer solution such as an aqueous solution, preferably a Hank's balanced salt solution, a Ringer's solution and a physiological salt buffer solution. Examples of optional components other than the pharmacologically and pharmaceutically acceptable carrier include a diluent, a solubilizer or a dissolution aid, a tonicity agent, a pH adjuster, a stabilizer, an antiseptic, a preservative, a dispersant, an emulsifier, a gelling agent, a thickener, a pressure-sensitive adhesive, and a dye.

The dosage form of the wound healing accelerator, etc. of the present invention is not particularly limited and is preferably a topical administration agent for topical administration to a wound site. Examples thereof more preferably include a liquid agent for external use (liniment, etc.), a spray (in the form of mist, powder, foam or paste), a patch (matrix tape, reserver tape, poultice, etc.), an ointment, a cream, a gel (collagen gel agent, CMC gel (sodium salt of carboxymethylcellulose or potassium salt of carboxymethylcellulose) agent, thermally responsive gel agent (e.g., an agent that is gelled by body temperature), etc.), and a solid agent for external use (liniment, powder, etc.), and even more preferably include a liquid agent for external use, a spray, a patch, and a gel.

The dose of the wound healing accelerator, etc. of the present invention per administration is not particularly limited as long as the wound healing accelerating effect is obtained. Those skilled in the art can appropriately set the dose in consideration of the degree, size, etc. of the wound of a patient. For example, $1 \times 10^5$ to $1 \times 10^{11}$ platelet-like cells of the present invention per administration can be used for a 1 cm suture wound. The number of doses of the wound healing accelerator, etc. of the present invention is not particularly limited as long as the wound healing accelerating effect is obtained. Even one dose thereof produces an excellent wound healing accelerating effect. Therefore, the number of doses may be one or may be two or more. Examples of two or more doses include 1 to 7, 1 to 5, 1 to 3, and 1 or 2. In the case of administering the wound healing accelerator, etc. of the present invention two or more times, examples of the interval of the administration period include, but are not particularly limited to, 1 to 3 days and 1 to 2 days.

Examples of the administration subject of the wound healing accelerator, etc. of the present invention include a vertebrate having a wound. Examples of the type of the vertebrate can include a mammal, a bird, a reptile, an amphibian, and fish. Among others, examples thereof can preferably include a mammal such as a human, a mouse, a rat, a guinea pig, a rabbit, a cat, a dog, a horse, cattle, a monkey, sheep, a goat, and a pig and can particularly preferably include a human.

(Method for Manufacturing Platelet-Like Cell Population of Present Invention)

The method for manufacturing the platelet-like cell population of the present invention is not particularly limited as long as the method involves culturing mesenchymal cells in a "medium for induction of differentiation into megakaryocytic cells" (hereinafter, referred to as the "medium used in the present invention") (preferably a modified medium for induction of differentiation into megakaryocytic cells) containing an iron ion and an iron transporter, and collecting the platelet-like cell population of the present invention from the culture product. In this context, the "medium" refers to matter in a state of water added to a "culture medium component" that can culture cells. When mesenchymal cells such as preadipocytes are cultured in the medium for induction of differentiation into megakaryocytic cells containing an iron ion and an iron transporter, the cells produce a platelet-like cell population under any mechanism. Although the details thereof are unknown, it is considered that the iron ion or the iron ion and the iron transporter taken up into the mesenchymal cells promote the secretion of thrombopoietin (TPO) from the cells under some mechanism, and this partly promotes the induction of differentiation into a platelet-like cell population from the cells.

The mesenchymal cell used in the present invention is not particularly limited as long as the mesenchymal cell is capable of producing a megakaryocyte or platelet by culture in a medium for induction of differentiation into megakaryocytic cells (preferably a modified medium for induction of differentiation into megakaryocytic cells) containing an iron ion and an iron transporter. Examples of the mesenchymal cell can include (a) a preadipocyte (or an adipose progenitor cell), (b) a mesenchymal stem cell, and (c) a stromal cell. Examples of the mesenchymal stem cell can include a subcutaneous adipose tissue-derived mesenchymal stem cell and a bone marrow mesenchymal stem cell. Examples of the stromal cell can include an adipose tissue-derived stromal cell, a bone marrow stromal cell, a prostate-derived stromal cell, and an endometrium-derived stromal cell. Preferred examples of the mesenchymal cell can include a preadipocyte and a subcutaneous adipose tissue-derived mesenchymal stem cell.

The mesenchymal cell used in the present invention may be a cultured cell line or may be a cell collected from a tissue (including a primary cultured cell and a successively cultured cell). More specific examples of the mesenchymal cell used in the present invention can include a human primary cultured preadipocyte (HPAd cell), a mouse primary cultured progenitor cell (subcutaneous adipose tissue-derived), an established mouse stromal cell line (OP9 cell), an established mouse bone marrow mesenchymal stem cell line (HS-22 cell), and an established mouse preadipocyte line (3T3-L1 cell).

A commercially available product from a company or the like, such as Lonza Group AG, PromoCell GmbH, Cell Applications, Inc., National Institute of Biomedical Innovation, or JCRB Cell Bank may be used as the cultured cell line of the mesenchymal cell or the mesenchymal cell collected from a tissue. Use of a mesenchymal cell collected from a tissue of an administration subject of the platelet-like cell population of the present invention does not cause immune rejection problems. Therefore, preferred examples thereof can include use of such a mesenchymal cell.

In the case of using a cultured cell line as the mesenchymal cell, an established line of a mesenchymal cell provided by collection from a tissue, etc. may be used. The method for establishing a line of the mesenchymal cell is not particularly limited, and a publicly known method or the like can be used. Preferred examples of the method for establishing a line of the preadipocyte can include a method which involves, as described in Example 1 mentioned later, inducing the differentiation of a preadipocyte into a mature adipocyte, and then applying a publicly known ceiling culture method as a method for establishing a line of the mature adipocyte, thereby obtaining a preadipocyte line. The established mesenchymal cell line thus obtained semipermanently maintains the ability to differentiate and the ability to proliferate and therefore has the advantage that, provided that the mesenchymal cell line is cryopreserved, for example, the manufacture of the platelet-like cell population of the present invention can be launched whenever the platelet-like cell population of the present invention is required.

The preadipocyte or the subcutaneous adipose tissue-derived mesenchymal stem cell described above can be collected from an adipose tissue such as a subcutaneous adipose tissue or a visceral tissue. The bone marrow mesenchymal stem cell can be collected from a bone marrow tissue. The stromal cell can be collected from an adipose tissue, a bone marrow tissue, the prostate, the endometrium, or the like. Preferred examples of the preadipocyte or the subcutaneous adipose tissue-derived mesenchymal stem cell can include an adipose tissue (preferably subcutaneous adipose tissue)-derived mesenchymal cell because of being low invasive upon collection and being capable of more conveniently collecting a larger number of mesenchymal cells. The method for collecting the mesenchymal cell from a tissue can employ a routine method.

The organism species from which the mesenchymal cell used in the present invention or the platelet-like cell population according to the present invention is derived is not particularly limited as long as the organism species is a vertebrate. Examples of the vertebrate can include a mammal, a bird, a reptile, an amphibian, and fish. Among others, examples thereof can preferably include a mammal such as a human, a mouse, a rat, a guinea pig, a rabbit, a cat, a dog, a horse, cattle, a monkey, sheep, a goat, and a pig and can particularly preferably include a human.

The medium used in the present invention is a medium for induction of differentiation into megakaryocytic cells (preferably a "modified medium for induction of differentiation into megakaryocytic cells") containing an iron ion and an iron transporter. The medium for induction of differentiation into megakaryocytic cells containing an iron ion and an iron transporter is a medium containing an iron ion and an iron transporter in a basal medium for mesenchymal cell culture that can culture mesenchymal cells. The iron ion and the iron transporter further contained therein cause the function of inducing the differentiation of mesenchymal cells into megakaryocytic cells.

The iron ion may be any of an iron ion(II) and an iron ion(III). Preferred examples thereof can include an iron ion(III). Examples of the method for allowing the iron ion to be contained in the medium for induction of differentiation into megakaryocytic cells can include a method of adding one or more iron salts selected from the group consisting of an inorganic salt and an organic salt of iron to the medium for induction of differentiation into megakaryocytic cells. The iron salt may be an organic salt or may be an inorganic salt. Examples of the inorganic salt can include iron(II) chloride, iron(III) chloride, iron(II) oxide, iron(III) oxide, iron(II) nitrate, iron(III) nitrate, iron(II) sulfate, iron(III) sulfate, ammonium iron(II) sulfate, ammonium iron(III) sulfate, iron(II) pyrophosphate, iron(III) pyrophosphate, iron(II) sulfide, iron(III) sulfide, iron(II) hydroxide, and iron(III) hydroxide. Examples of the organic salt can include iron(II) acetate, iron(III) acetate, hydroxy diacetoxy iron (III), iron(II) citrate, iron(III) citrate, sodium iron(III) citrate, ammonium iron(III) citrate, iron(II) benzoate, iron(III) benzoate, iron(II) carbonate, iron(III) carbonate, iron(II) formate, iron(III) formate, iron(II) oxalate, iron(III) oxalate, iron(II) fumarate, iron(III) fumarate, iron(II) succinate, iron (III) succinate, iron(II) gluconate, iron(III) gluconate, iron (II) lactate, iron(III) lactate, iron(II) maleate, iron(III) maleate, sodium iron(III) diethylenetriaminepentaacetate, ammonium iron(III) diethylenetriaminepentaacetate, sodium iron(III) ethylenediaminetetraacetate, ammonium iron(III) ethylenediaminetetraacetate, sodium iron(III) dicarboxymethylglutamate, and ammonium iron(III) dicarboxymethylglutamate. These iron salts may each be used alone or may be used in combination of two or more thereof. Commercially available products can be used as these iron salts.

The iron transporter binds to the iron ion contained in the medium used in the present invention and thereby provides the mesenchymal cell with the uptake ability of the iron ion from the medium. An iron transporter bound with an iron ion, if used, also functions as a supply source of iron. The iron transporter may be called apo form when not bound with iron, called holo form when bound with iron, and called sidero form when bound with iron in an amount at an intermediate level between the apo form and the holo form. Examples of the iron transporter can include a protein that is taken up into a cell by binding to iron (Japanese unexamined Patent Application Publication No. 08-029429, Japanese unexamined Patent Application Publication (Translation of PCT Application) No. 2005-517042, Japanese unexamined Patent Application Publication (Translation of PCT Application) No. 2004-505932, Japanese unexamined Patent Application Publication (Translation of PCT Application) No. 2007-508026, etc.). The apo form or an iron transporter corresponding thereto includes apotransferrin (apo-serotransferrin), apolactoferrin, apo-ovotransferrin, apo-melanotransferrin, apoferritin, protoporphyrin IX and the like. Among others, preferred examples thereof can include apotransferrin. The same organism species as that from which the mesenchymal cell used with the iron transporter is derived is preferably used as the organism species from which the iron transporter is derived.

A complex formed by the binding between the iron ion and the iron transporter (iron ion-iron transporter complex) can be preferably used as the iron ion and the iron transporter according to the present invention. Examples of the iron ion-iron transporter complex can include holotransferrin (iron-bound transferrin) in which apotransferrin is bound with an iron ion, hololactoferrin (iron-bound lactoferrin) in which apolactoferrin is bound with an iron ion, holo-ovotransferrin (iron-bound ovotransferrin) in which apo-ovotransferrin is bound with an iron ion, holo-melanotransferrin (iron-bound melanotransferrin) in which apo-melanotransferrin is bound with an iron ion, holoferritin (iron-bound ferritin) in which apoferritin is bound with an iron ion, and hem in which protoporphyrin IX is bound with iron. Among others, preferred examples thereof can include iron-bound transferrin. Commercially available products can be used as the iron transporter in a holo form bound with the iron ion, the iron transporter in an apo form not bound with the iron ion, and the iron transporter in a sidero form bound with iron in an amount at an intermediate level between the apo form and the holo form.

The binding pattern between the iron ion and the iron transporter in the iron ion-iron transporter complex described above is not particularly limited and may be a noncovalent bond such as a coordinate bond, an ionic bond, a hydrogen bond, a metal bond, or van der Waals' force or may be a covalent bond. Preferred examples thereof can include a coordinate bond because of being a moderate degree of binding and being suitable for transporting the iron ion into the mesenchymal cell. Although iron is not in an ion state in the iron ion-iron transporter complex, the iron ion-iron transporter complex according to the present invention also includes, for the sake of convenience, a complex capable of releasing an iron ion upon uptake into the mesenchymal cell.

The concentration of the iron ion in the medium used in the present invention is not particularly limited as long as the medium used in the present invention having such an iron concentration is a medium capable of manufacturing the platelet-like cell population of the present invention by the culture of the mesenchymal cell. Examples thereof can include a concentration within the range of 1 pg/mL to 10 µg/mL, preferably within the range of 10 pg to 1 µg/mL, more preferably within the range of 150 pg/mL to 300 pg/mL, even more preferably within the range of 150 pg/mL to 250 pg/mL.

The content of the iron transporter in the medium used in the present invention is not particularly limited as long as the medium used in the present invention having such a content of the iron transporter is a medium capable of manufacturing the platelet-like cell population of the present invention by the culture of the mesenchymal cell. Examples thereof can include a content within the range of 10 fM ($1 \times 10^{-15}$ M) to 100 nM, preferably within the range of 100 fM to 10 nM, more preferably within the range of 1 pM to 2.8 pM, even more preferably within the range of 1 pM to 2.5 pM.

In the case of using iron-bound transferrin in the medium used in the present invention, the addition concentration thereof is not particularly limited and may abide by the numeric range of the iron ion concentration described above. Examples thereof can include 25 µg/mL to less than 400 µg/mL, preferably 50 µg/mL to less than 200 µg/mL. 1 mg of iron-bound transferrin reportedly contains approximately 1.3 µg of the bound iron ion.

The medium for induction of differentiation into megakaryocytic cells according to the present invention is not particularly limited as long as the medium, when the iron ion and the iron transporter according to the present invention are added thereto, is a medium capable of manufacturing the platelet-like cell population of the present invention by the culture of the mesenchymal cell. A chemically synthesized medium is preferred because of being easily prepared and preventing lot-to-lot variations. The medium preferably contains one or more types of saccharides, one or more types of inorganic salts, one or more types of amino acids, and one or more types of vitamins, and one or more types of additional components.

Specific examples of the saccharide can include: a monosaccharide such as glucose, mannose, fructose, and galactose; and a disaccharide such as sucrose, maltose, and lactose. Among them, glucose is particularly preferred. One of or two or more in combination of these saccharides can be added.

Specific examples of the inorganic salt can include one or more inorganic salts selected from calcium chloride, calcium nitrate, copper sulfate pentahydrate, iron(III) nitrate nonahydrate, iron(II) sulfate heptahydrate, magnesium chloride hexahydrate, magnesium sulfate, potassium chloride, sodium chloride, sodium bicarbonate, disodium hydrogen phosphate, disodium hydrogen phosphate dihydrate, sodium dihydrogen phosphate, sodium dihydrogen phosphate monohydrate, sodium dihydrogen phosphate dihydrate, sodium selenite pentahydrate, and zinc sulfate heptahydrate. Any of these inorganic salts or any combination thereof can be used as long as the component acts advantageously on the production of the platelet-like cell population from the mesenchymal cell.

Specific examples of the amino acid can include one or more amino acids selected from alanine, arginine, asparagine, aspartic acid, cystine, cysteine, glutamine, glycine, histidine, glutamic acid, hydroxyproline, isoleucine, leucine, lysine, methionine, phenylalanine, proline, serine, threonine, tryptophan, tyrosine, valine, and the like, preferably a L-amino acid and its analog such as a derivative thereof and a salt thereof, and a hydrate thereof. Examples of the arginine can include an arginine analog such as L-arginine hydrochloride and L-arginine monohydrochloride. Examples of the aspartic acid can include an aspartic acid analog such as L-aspartic acid sodium salt monohydrate, L-aspartic acid monohydrate, potassium L-aspartate, and magnesium L-aspartate. Examples of the cysteine can include a cysteine analog such as L-cysteine dihydrochloride and L-cysteine hydrochloride monohydrate. Examples of the glutamic acid can include a glutamic acid analog such as L-glutamic acid monosodium salt. Examples of the asparagine can include an asparagine analog such as L-asparagine monohydrate. Examples of the tyrosine can include a tyrosine analog such as L-tyrosine disodium dihydrate. Examples of the histidine can include a histidine analog such as histidine hydrochloride and histidine hydrochloride monohydrate. Examples of the lysine can include a lysine analog such as L-lysine hydrochloride.

Specific examples of the vitamin can include one or more vitamins selected from biotin, choline, folic acid, inositol, niacin, pantothenic acid, pyridoxine, riboflavin, thiamine, vitamin B12, para-aminobenzoic acid (PABA), and ascorbic acid, and their analogs such as respective derivatives of these components and salts thereof, and hydrates thereof. Examples of the choline can include a choline analog such as choline chloride. Examples of the niacin can include a niacin analog such as nicotinic acid, nicotinic acid amide, and nicotinic alcohol. Examples of the pantothenic acid can include a pantothenic acid analog such as calcium pantothenate, sodium pantothenate, and panthenol. Examples of the pyridoxine can include a pyridoxine analog such as pyridoxine hydrochloride, pyridoxal hydrochloride, pyridoxal phosphate, and pyridoxamine. Examples of the thiamine can include a thiamine analog such as thiamine hydrochloride, thiamine nitrate, bisthiamine nitrate, thiamine dicetyl sulfuric acid ester salt, fursultiamine hydrochloride, octotiamine, and benfotiamine. Examples of the ascorbic acid can include an ascorbic acid analog such as ascorbic acid 2-phosphate, magnesium ascorbyl phosphate, sodium ascorbyl sulfate, aminopropyl ascorbyl phosphate, and sodium ascorbyl phosphate.

Examples of the additional component can include a buffer such as HEPES, a nucleic acid such as a nucleotide, an antibiotic such as penicillin and streptomycin, pyruvic acid, and their analogs such as derivatives thereof and salts thereof, and hydrates thereof, and Phenol Red. Preferred examples of the nucleotide can include ATP, UTP, GTP, and CTP, preferably an equimolar mixture of these four nucleotides. Preferred example of the analog of the antibiotic can include penicillin G sodium, streptomycin sulfate, and a penicillin-streptomycin solution. Preferred examples of the analog of the pyruvic acid can include sodium pyruvate.

As mentioned above, the medium for induction of differentiation into megakaryocytic cells is a medium containing an iron ion and an iron transporter in a basal medium for mesenchymal cell culture that can culture mesenchymal cells. Specific examples of the basal medium for mesenchymal cell culture can preferably include: a publicly known chemically synthesized medium such as commercially available Iscove's Modified Dulbecco's Medium (IMDM), RPMI 1640 medium, Dulbecco's modified eagle's medium (DMEM), minimum essential medium (MEM), Basal Medium Eagle (BME), and F12 medium; a medium in which any two or more of these media are mixed at an appropriate ratio, such as DMEM/F12 medium (medium of DMEM and F12 medium mixed at a ratio of 1:1); and a medium in which a nucleic acid such as a nucleotide, an antibiotic such as penicillin or streptomycin, and L-glutamine are further added to any of these media, and particularly, can more preferably include a medium in which an antibiotic (preferably penicillin G sodium, streptomycin sulfate, or a penicillin-streptomycin solution) and L-glutamine are further added to IMDM or RPMI 1640 medium. Among others, particularly preferred examples thereof can include a medium in which an antibiotic (preferably penicillin G sodium, streptomycin sulfate, or a penicillin-streptomycin solution) and L-glutamine are further added to IMDM.

Particularly preferred examples of the basal medium for mesenchymal cell culture according to the present invention can include a medium in which 2 mM (final concentration) L-glutamine and 100 U/mL (final concentration) penicillin-streptomycin solution are added to IMDM having a formulation mentioned later (hereinafter, referred to as the "particularly preferred basal medium according to the present invention"), and a medium containing each component having a concentration at a proportion within the range of 70 to 130% by weight (preferably within the range of 80 to 120% by weight) of each component independently with respect to the concentration of each component in the particularly preferred basal medium according to the present invention.

(Formulation of IMDM)

0.4 mM glycine, 0.281 mM L-alanine, 0.398 mM L-arginine hydrochloride, 0.167 mM L-asparagine, 0.226 mM L-aspartic acid, 0.381 mM L-cystine dihydrochloride, 0.51 mM L-glutamic acid, 4 mM L-glutamine, 0.2 mM L-histidine hydrochloride monohydrate, 0.802 mM L-isoleucine, 0.802 mM L-leucine, 0.798 mM L-lysine hydrochloride, 0.201 mM L-methionine, 0.4 mM L-phenylalanine, 0.348 mM L-proline, 0.4 mM L-serine, 0.798 mM L-threonine, 0.0784 mM L-tryptophan, 0.462 mM L-tyrosine disodium dihydrate, 0.803 mM L-valine, 0.0000533 mM biotin, 0.0286 mM choline chloride, 0.00839 mM calcium D-pantothenate, 0.00907 mM folic acid, 0.0328 mM nicotinic acid amide, 0.0196 mM pyridoxal hydrochloride, 0.00106 mM riboflavin, 0.119 mM thiamine hydrochloride, 0.0000096 mM vitamin B12, 0.04 mM i-inositol, 1.49 mM anhydrous calcium chloride, 0.84 mM anhydrous magnesium sulfate, 4.4 mM potassium chloride, 0.000752 mM potassium nitrate, 36 mM sodium bicarbonate, 77.59 mM sodium chloride, 0.906 mM sodium dihydrogen phosphate monohydrate, 0.0000658 mM sodium selenite pentahydrate, 25 mM D-glucose, 25.03 mM HEPES, 0.0399 mM Phenol Red, and 1 mM sodium pyruvate.

Particularly preferred examples of the medium used in the present invention can include a medium containing an iron ion and an iron transporter in the particularly preferred basal medium according to the present invention mentioned above. Among others, more preferred examples thereof can include a medium containing iron-bound transferrin as a single active ingredient in the particularly preferred basal medium according to the present invention mentioned above.

TPO, bovine serum albumin (BSA), LDL cholesterol, insulin, 2-β-mercaptoethanol, or the like may be added to the medium used in the present invention. The case of not adding these components is of greater significance in such a way that the platelet-like cell population of the present invention can be manufactured at a lower cost. Specifically, MKLI medium, which has conventionally been used as a medium for induction of differentiation into megakaryocytic cells, contains TPO, BSA, LDL cholesterol, insulin and 2-β-mercaptoethanol (hereinafter, these components are also collectively referred to as "5 components") added to IMDM medium (Matsubara Y, Murata M, Ikeda Y., Culture of megakaryocytes and platelets from subcutaneous adipose tissue and a preadipocyte cell line, Methods Mol Biol. 2012; 788: 249-258). In the case of not using these 5 components in the medium used in the present invention, the platelet-like cell population of the present invention can be manufactured at a lower cost. The present inventors have experimentally confirmed that the induction of differentiation of preadipocytes into megakaryocytes or platelet does not require any of BSA, LDL cholesterol, insulin and 2-β-mercaptoethanol. As for the medium used in the present invention (i.e., the "medium for induction of differentiation into megakaryocytic cells containing an iron ion and an iron transporter"), a medium that is free from bovine serum albumin, LDL cholesterol, deoxyribonucleotide triphosphate, and 2-mercaptoethanol and contains human serum albumin, iron-bound transferrin, insulin, and monothioglycerol is referred to as a "modified medium for induction of differentiation into megakaryocytic cells" in the present specification. When the mesenchymal cell can take up the iron ion in the medium into the cell even in the absence of the iron transporter in the medium, the medium used in the present invention can also be prepared as a "medium for induction of differentiation into megakaryocytic cells containing an iron ion", rather than the "medium for induction of differentiation into megakaryocytic cells containing an iron ion and an iron transporter".

In a particularly preferred aspect, examples of the medium used in the present invention include a medium in which human serum albumin, iron-bound transferrin, insulin, and monothioglycerol are added to the particularly preferred basal medium according to the present invention mentioned above and further include a medium in which such a medium is free from bovine serum albumin, LDL cholesterol, deoxyribonucleotide triphosphate, and 2-mercaptoethanol. More specific examples thereof can include a modified MKLI medium of Example 2 mentioned later, and a medium containing each component having a concentration at a proportion within the range of 70 to 130% by weight (preferably within the range of 80 to 120% by weight) of each component independently with respect to the concentration of each component in the medium. The modified MKLI medium of Example 2 mentioned later, and the medium containing each component having a concentration at a proportion within the range of 70 to 130% by weight (preferably within the range of 80 to 120% by weight) of each component independently with respect to the concentration of each component in the medium is preferably included in the "modified medium for induction of differentiation into megakaryocytic cells". The modified MKLI medium differs from the conventional MKLI medium in using human serum albumin instead of BSA, in not using LDL cholesterol, in not using dNTP, and in using monothioglycerol instead of mercaptoethanol.

The culture conditions according to the present invention are not particularly limited as long as the platelet-like cell population of the present invention can be manufactured by the culture of the mesenchymal cell in the medium used in the present invention. Examples of the culture temperature can include a temperature usually within the range of 12 to 45° C., preferably within the range of 15 to 37° C. Examples of the culture period can include a period usually within the range of 4 to 25 days, preferably within the range of 5 to 17 days. Examples of the culture period can also include a period within the range of 8 to 17 days.

Preferably, the manufacture method of the present invention further has the step of increasing a cell count by the maintenance culture of the mesenchymal cell before the culture of the mesenchymal cell used in the present invention in the medium used in the present invention. This is because, as mentioned later, the maintenance culture step can increase the count of the mesenchymal cell that can be used in the culture in the medium used in the present invention and can drastically elevate the yield of the platelet-like cell population of the present invention with respect to the initially provided mesenchymal cell count. The medium for use in the maintenance culture is not particularly limited as long as the medium permits proliferation of the mesenchymal cell used in the present invention. Examples thereof can include the basal medium for mesenchymal cell culture (containing neither an iron ion nor an iron transporter) mentioned above. In the case of performing maintenance culture, it is preferred to use a basal medium for mesenchymal cell culture containing serum or a serum component. In the maintenance culture step, it is preferred to appropriately perform subculture or medium replacement.

Examples of the method for collecting the platelet-like cell population of the present invention from the culture product according to the present invention can include, but are not particularly limited to, a method of preparatively separating a culture supernatant containing the platelet-like cell population of the present invention from the culture product, and a method of separating the platelet-like cell population of the present invention depending on the size of a molecule using a filter or the like.

The method for manufacturing the platelet-like cell population of the present invention may further comprise the step of (a) selecting a platelet-like cell having a particular cell surface marker profile (i.e., a platelet-like cell expressing a particular cell surface marker or a particular combination of cell surface markers) from the platelet-like cell population of the present invention, or (b) improving or reducing a proportion of a platelet-like cell having a particular cell surface marker profile in the platelet-like cell population of the present invention, by using the presence or absence of the particular cell surface marker or the particular combination of cell surface markers as an index, at the time of or after the collection of the platelet-like cell population of the present invention from the culture product. It is preferred that the manufacture method of the present invention should be free from such a step, from the viewpoint of convenience, etc. In the platelet-like cell population that has undergone the selection step or the improvement or reduction step, the proportion of a platelet-like cell expressing a particular cell surface marker or a particular combination of cell surface markers includes each of the proportions of cells positive to particular cell surface markers listed in the present specification, or every combination of the proportions.

Preferred examples of the method for (a) selecting a platelet-like cell having a particular cell surface marker profile from the platelet-like cell population of the present invention, or the method for (b) improving or reducing a proportion of a platelet-like cell having a particular cell surface marker profile in the platelet-like cell population of the present invention can include, but are not particularly limited to, a method of using an antibody (preferably a labeled antibody, more preferably a fluorescently labeled antibody) against each cell surface marker described above, and selecting a platelet-like cell population having the particular cell surface marker profile by using the presence or absence of the specific binding of the antibody as an index, from the viewpoint of more conveniently and rapidly selecting a platelet-like cell having the target cell surface marker profile, or from the viewpoint of improving or reducing a proportion of a platelet-like cell having the target cell surface marker profile.

The phrase "selecting by using the presence or absence of the specific binding of the antibody as an index" means that: as to a cell surface marker resulting in positivity in the profile, a cell to which the antibody against the marker exhibits specific binding is selected; and as to a cell surface marker resulting in negativity in the profile, a cell to which the antibody against the marker exhibits no specific binding is selected. Examples of the method for selecting a mesenchymal cell having the particular cell surface marker profile by using the presence or absence of the specific binding of the antibody as an index can include, but are not particularly limited to, a method using a cell sorter, magnetic beads or a column for cell adsorption. Preferred examples thereof can include a method using a cell sorter because of being more convenient and rapid. The method using a cell sorter is based on flow cytometry and well known to those skilled in the art. The method is specifically described in an instruction manual of the cell sorter as well as Japanese unexamined Patent Application Publication (Translation of PCT Application) No. 2009-513161, etc. The method using magnetic beads is well known as a magnetic separation method or the like to those skilled in the art. Specific examples of the method can include a method of contacting magnetic beads carrying a particular antibody with cells, and then collecting the magnetic beads with a magnet, thereby separating a cell specifically binding to the particular antibody. The method using a column for cell adsorption is well known to those skilled in the art. Specific examples of the method can include a method of contacting a cell group with a column for cell adsorption carrying a particular antibody to adsorb a cell other than the target cell onto the column.

In a particularly preferred aspect, examples of the method for manufacturing the platelet-like cell population of the present invention include a method for manufacturing the platelet-like cell population of the present invention, comprising the steps of:

(A) inducing the differentiation of one or more cells selected from a stromal vascular fraction including a mesenchymal stem cell, a preadipocyte and a stromal cell of a vertebrate adipose tissue into a mature adipocyte;

(B) inducing the dedifferentiation of the mature adipocyte obtained in the step (A) to obtain a vertebrate adipose tissue-derived mesenchymal cell line; and (C) culturing the adipose tissue-derived mesenchymal cell line obtained in the step (B) in a modified medium for induction of differentiation into megakaryocytic cells containing an iron ion and an iron transporter, and collecting a platelet-like cell population from the culture product, wherein the modified medium for induction of differentiation into megakaryocytic cells in the step (C) is free from bovine serum albumin, LDL cholesterol, deoxyribonucleotide triphosphate, and 2-mercaptoethanol and contains human serum albumin, iron-bound transferrin, insulin, and monothioglycerol. The platelet-like cell population manufactured by the manufacture method is particularly preferred as the platelet-like cell population of the present invention.

In a particularly preferred aspect, the method for manufacturing the platelet-like cell population of the present invention preferably further has any or both of the following features from the viewpoint of convenience and of obtaining a much better wound healing accelerating effect:

after obtaining the adipose tissue-derived mesenchymal cell line in the step (B) and before culturing the cell line in the modified medium for induction of differentiation into megakaryocytic cells containing an iron ion and an iron transporter in the step (C), a selection of a cell by using the presence or absence of an expression of a particular cell surface marker as an index is not performed for the cell line; and in the step (C), the method for collecting the platelet-like cell population from the culture product does not comprise selection of a cell by using the presence or absence of an expression of a particular cell surface marker as an index.

(Step A)

The step (A) described above is not particularly limited as long as the step involves inducing the differentiation of one or more cells (hereinafter, also referred to as a "mesenchymal stem cell, etc." in the present specification) selected from a stromal vascular fraction including a mesenchymal stem cell, a preadipocyte and a stromal cell of a vertebrate adipose tissue into a mature adipocyte. The differentiation induction step is an ex vivo differentiation induction step.

The organism species from which the adipose tissue is derived is not particularly limited as long as the organism species is a vertebrate. Examples thereof can include a mammal, a bird, a reptile, an amphibian, and fish. Among others, examples thereof can preferably include a mammal such as a human, a mouse, a rat, a guinea pig, a rabbit, a cat, a dog, a horse, cattle, a monkey, sheep, a goat, and a pig and can particularly preferably include a human. The organism species of the vertebrate from which the adipose tissue for use in the method for manufacturing the platelet-like cell population of the present invention is derived is preferably the same as the organism species of the vertebrate to which the wound healing accelerator of the present invention is to be applied, from the viewpoint of avoiding rejection reaction or the like.

In the present specification, the "adipose tissue" is not particularly limited as long as the tissue contains adipose. Examples thereof include a subcutaneous adipose tissue, an adipose tissue in bone marrow, and a visceral adipose tissue. Preferred examples thereof include a subcutaneous adipose tissue because of being relatively low invasive to the vertebrate that supplies the adipose tissue and being also relatively easily collected.

In the present specification, the "stromal vascular fraction" means cells other than a mature adipocyte among cells of the vertebrate adipose tissue. The stromal vascular fraction usually includes cells such as a mesenchymal stem cell, a preadipocyte, a stromal cell, a vascular endothelial cell, a hematological cell, a smooth muscle cell, and a fibroblast. The "stromal vascular fraction" can be obtained by removing a mature adipocyte from a cell population obtained by the processing of the vertebrate adipose tissue with an enzyme capable of dissociating vertebrate adipose tissue cells.

The "one or more cells selected from a stromal vascular fraction including a mesenchymal stem cell, a preadipocyte and a stromal cell of a vertebrate adipose tissue" are not particularly limited as long as the one or more cells are selected from a stromal vascular fraction including a mesenchymal stem cell, a preadipocyte (or an adipose progenitor cell) and a stromal cell of a vertebrate adipose tissue. These cells are preferably a cell population comprising at least a preadipocyte, a mesenchymal stem cell and/or a stromal cell, more preferably a cell population comprising at least a preadipocyte, a mesenchymal stem cell and a stromal cell, from the viewpoint of more efficiently manufacturing a vertebrate adipose tissue-derived mesenchymal cell line, further preferably a cell population of a stromal vascular fraction from the viewpoint of more convenient preparation, rather than a cell population of only a preadipocyte.

In a preferred aspect, examples of the "one or more cells selected from a stromal vascular fraction including a mesenchymal stem cell, a preadipocyte and a stromal cell of a vertebrate adipose tissue" include one or more cells selected from a stromal vascular fraction including a mesenchymal stem cell, a preadipocyte and a stromal cell obtained by cell dissociation of the vertebrate adipose tissue. Among others, preferred examples thereof include a cell population (cell population A) obtained by removing a mature adipocyte from a cell population obtained by the processing of the vertebrate adipose tissue with an enzyme capable of dissociating vertebrate adipose tissue cells. A cell population obtained by further removing a vascular endothelial cell and/or a hematological cell from the cell population A may be used. The cells (cell population A) obtained by removing a mature adipocyte, etc. from a cell population obtained by the processing of the vertebrate adipose tissue with an enzyme capable of dissociating vertebrate adipose tissue cells as mentioned above is a cell population of a stromal vascular fraction. The stromal vascular fraction usually includes cells such as a mesenchymal stem cell, a preadipocyte, a stromal cell, a vascular endothelial cell, a hematological cell, a smooth muscle cell, and a fibroblast of the vertebrate adipose tissue.

Examples of the method for the "processing of the vertebrate adipose tissue with an enzyme capable of dissociating vertebrate adipose tissue cells" include a method of dipping the vertebrate adipose tissue in a solution containing the enzyme, followed by incubation for, for example, approximately 30 minutes to 3 hours.

The "enzyme capable of dissociating vertebrate adipose tissue cells" is not particularly limited as long as the enzyme can dissociate cells of the vertebrate adipose tissue by acting on the vertebrate adipose tissue. Examples thereof include one or more enzymes selected from the group consisting of collagenase, trypsin, caseinase, clostripain, trypsin-EDTA, Dispase, thermolysin, pronase, hyaluronidase, pancreatin, elastase and papain. Among others, examples thereof preferably include one or more enzymes selected from the group consisting of collagenase, trypsin, caseinase and clostripain, more preferably include commercially available collagenase (type I) and collagenase (type II), and even more preferably include collagenase (type II). The "enzyme capable of dissociating vertebrate adipose tissue cells" also preferably comprises at least collagenase.

The method for "removing a mature adipocyte from a cell population obtained by the processing of the vertebrate adipose tissue with an enzyme capable of dissociating vertebrate adipose tissue cells" is not particularly limited as long as the method can remove a mature adipocyte from the cell population. Preferred examples thereof include a method of collecting a cell population (cell pellets) precipitated during centrifugation of a suspension containing the cell population mentioned above. Since the mature adipocyte is rich in adipose, the mature adipocyte has a small specific gravity and floats in the upper portion of a supernatant after centrifugation. Therefore, the mature adipocyte can be removed by collecting cell pellets precipitated by the centrifugation. The method for removing a vascular endothelial cell, a smooth muscle cell, and a fibroblast from the cell population obtained by the processing of the vertebrate adipose tissue with an enzyme capable of dissociating vertebrate adipose tissue cells is not particularly limited as long as the method can remove these cells from the cell population. Examples thereof include a method of removing a vascular endothelial cell from the cell population by selecting a cell negative to CD31 known as a vascular endothelial cell marker (or removing a cell positive to CD31). Examples of the method for removing a hematological cell from the cell population include a method of removing a hematological cell from the cell population by selecting a CD45 (marker of a hematopoietic cell other than an erythrocyte and platelet)-negative and Ter119 (marker of an erythrocyte or its progenitor cell)-negative cell (or removing a CD45-positive and Ter119-positive cell). It is preferred to use negativity to 7-amino-actinomycin D (7-AAD), albeit not a cell surface marker, as an index, because dead cells contained in the vertebrate adipose tissue can be eliminated. 7-AAD intercalates into the DNA strand of a dead cell and emits red fluorescence by excitation light of 488 nm.

The precipitated cell pellets (cell population A) described above are cells of a stromal vascular fraction. The stromal vascular fraction usually includes a mesenchymal stem cell, a preadipocyte, a stromal cell (stroma cell), a vascular endothelial cell, a smooth muscle cell, a fibroblast, and the like. Among these cells, cells capable of differentiating into a mature adipocyte are a mesenchymal stem cell, a preadipocyte, and a stromal cell. Thus, the manufacture method of the present invention may further have the step of removing any one or more of or all types of cells other than these 3 cells from the precipitated cell pellets described above, for example, before induction of the differentiation into a mature adipocyte, or may not have such a step. It is preferred that the manufacture method of the present invention should not have such a step, from the viewpoint of the convenience of operation. The vascular endothelial cell, the smooth muscle cell, and the fibroblast, even if subjected to the induction of differentiation into a mature adipocyte together with the mesenchymal stem cell, etc., neither differentiate into a mature adipocyte nor interfere with the differentiation of the mesenchymal stem cell, etc. into a mature adipocyte.

In the step (A) described above, preferred examples of the method for inducing the differentiation of one or more cells selected from a stromal vascular fraction including a mesenchymal stem cell, a preadipocyte and a stromal cell of a vertebrate adipose tissue into a mature adipocyte include a method of culturing one or more cells selected from a stromal vascular fraction including a mesenchymal stem cell, a preadipocyte and a stromal cell of a vertebrate adipose tissue in a basal medium for mesenchymal cell culture containing an adipocyte differentiation inducer. The method for culturing the mesenchymal stem cell, etc. in a basal medium for mesenchymal cell culture containing an adipocyte differentiation inducer is not particularly limited as long as the culture is capable of inducing the differentiation of the mesenchymal cell into a mature adipocyte. A method similar to, for example, a usual method for inducing the differentiation of a preadipocyte into a mature adipocyte, i.e., a method of culturing a starting cell in a basal medium for mesenchymal cell culture containing an adipocyte differentiation inducer, can be used.

In the step (A) described above, examples of the conditions, etc. for culturing the mesenchymal stem cell, etc. in a basal medium for mesenchymal cell culture containing an adipocyte differentiation inducer can include a method of performing adherent culture in a culture container coated with extracellular matrix. Examples of the culture temperature can include a temperature usually within the range of 12 to 45° C., preferably within the range of 15 to 37° C. Examples of the culture period can include a culture period within the range of 5 to 16 days, preferably within the range of 7 to 14 days, more preferably within the range of 8 to 12 days, even more preferably within the range of 9 to 11 days, still more preferably 10 days, from the viewpoint of the balance between more efficient manufacture of a vertebrate adipose tissue-derived mesenchymal cell line and manufacture in a shorter period. In the culture, the mesenchymal stem cell, etc. may not be subcultured or may be subcultured. Examples of the extracellular matrix include one or more components selected from collagen, fibronectin, proteoglycan, and laminin. For example, BD Matrigel® (manufactured by BD Biosciences) containing the component may be used.

The adipocyte differentiation inducer described above is not particularly limited as long as the adipocyte differentiation inducer has the function of allowing a cell whose differentiation into a mature adipocyte is inducible to differentiate into a mature adipocyte, or the function of assisting in this function. Examples thereof include one or more members selected from the group consisting of dexamethasone, isobutylmethylxanthine, insulin and serum. Among others, examples thereof preferably include a "combination of serum and dexamethasone", a "combination of adipocyte differentiation inducers comprising at least serum and dexamethasone", a "combination of serum and isobutylmethylxanthine", and a "combination of adipocyte differentiation inducers comprising at least serum and isobutylmethylxanthine", more preferably include a "combination of serum, dexamethasone and insulin", a "combination of adipocyte differentiation inducers comprising at least serum, dexamethasone and insulin", a "combination of serum, isobutylmethylxanthine and insulin", a "combination of adipocyte differentiation inducers comprising at least serum, isobutylmethylxanthine and insulin", a "combination of serum, dexamethasone and isobutylmethylxanthine", and a "combination of adipocyte differentiation inducers comprising at least serum, dexamethasone and isobutylmethylxanthine", and even more preferably include a "combination of serum, dexamethasone, isobutylmethylxanthine and insulin" and a "combination of adipocyte differentiation inducers comprising at least serum, dexamethasone, isobutylmethylxanthine and insulin", from the viewpoint of obtaining much better induction efficiency of differentiation into a mature adipocyte. A commercially available product may be used as the adipocyte differentiation inducer or the basal medium for mesenchymal cell culture containing the inducer. The medium may employ a medium prepared by adding the adipocyte differentiation inducer to a basal medium for mesenchymal cell culture. Preferred examples of the commercially available medium containing the adipocyte differentiation inducer include a medium Adipocyte Differentiation Medium (manufactured by Cell Applications, Inc.). Examples of a substance other than the adipocyte differentiation inducer listed above, the substance having the function of assisting in the function of causing differentiation into a mature adipocyte include rosiglitazone, pioglitazone, and indomethacin.

The concentration of the adipocyte differentiation inducer described above in the medium is not particularly limited as long as the differentiation of the mesenchymal stem cell, etc. into a mature adipocyte can be induced. Examples of the dexamethasone concentration include a concentration usually within the range of 0.1 to 10 μM, preferably within the range of 0.5 to 2.5 μM. Examples of the isobutylmethylxanthine concentration include a concentration within the range of 10 to 1000 μM, preferably within the range of 250 to 750 μM. Examples of the insulin concentration include a concentration within the range of 0.1 to 10 μM, preferably within the range of 0.5 to 2.5 μM. Examples of the serum concentration include a concentration within the range of 1 to 20% by weight, preferably within the range of 5 to 15% by weight, more preferably within the range of 7 to 13% by weight.

(Step B)

The step (B) described above is not particularly limited as long as the step involves inducing the dedifferentiation of the mature adipocyte (easy-to-dedifferentiate mature adipocyte) obtained in the step (A) to obtain a vertebrate adipose tissue-derived mesenchymal cell line. This step is an ex vivo step.

The mature adipocyte for use in the step (B) is the mature adipocyte obtained by the induction of differentiation in the step (A). The mature adipocyte can be obtained, for example, by centrifuging the culture suspension of the step (A), and collecting a cell floating in the upper portion of a supernatant. This is because, since the mature adipocyte is rich in adipose, the mature adipocyte has a small specific gravity and floats in the upper portion of a supernatant after centrifugation.

In the step (B) described above, the method for inducing the dedifferentiation of the mature adipocyte (easy-to-dedifferentiate mature adipocyte) obtained in the step (A) to obtain a vertebrate adipose tissue-derived mesenchymal cell line is not particularly limited as long as the method involves inducing the dedifferentiation of the mature adipocyte to obtain a vertebrate adipose tissue-derived mesenchymal cell line. Preferred examples thereof include a method of performing so-called ceiling culture of the mature adipocyte. The ceiling culture is a method of culturing a cell while allowing the cell to adhere to or float in (preferably adhere to) the upper inner surface (ceiling surface) of a culture container (preferably a culture flask) filled with a medium. This method cultures the cell through the use of the property of the mature adipocyte of having a small specific gravity and floating in a medium because of being rich in adipose.

Examples of the medium for inducing the dedifferentiation of the mature adipocyte by culture include a basal medium for mesenchymal cell culture containing extracellular matrix. Examples of the extracellular matrix include one or more components selected from collagen, fibronectin, proteoglycan, laminin, and serum (FBS, etc.). For example, BD Matrigel® (manufactured by BD Biosciences) containing the component may be used. The serum such as FBS in the medium for inducing the dedifferentiation of the mature adipocyte by culture may be used only as an adhesion factor for allowing the mature adipocyte to adhere to the ceiling surface of a culture container, or may not be used only as an adhesion factor therefor. The medium for inducing the dedifferentiation of the mature adipocyte by culture may be free from serum such as FBS and preferably contains serum such as FBS together with extracellular matrix other than serum or without extracellular matrix other than serum, from the viewpoint of more efficiently manufacturing a vertebrate adipose tissue-derived mesenchymal cell line. When the medium contains serum such as FBS, the serum concentration is not particularly limited as long as the vertebrate adipose tissue-derived mesenchymal cell line can be obtained. Examples thereof include a concentration within the range of 3 to 30% by weight, preferably within the range of 7 to 25% by weight, more preferably within the range of 7 to 13% by weight.

In the step (B) described above, conditions, etc. other than ceiling culture among the conditions, etc. for culturing the mature adipocyte in a basal medium for mesenchymal cell culture containing extracellular matrix will be mentioned.

Examples of the culture temperature can include a temperature usually within the range of 12 to 45° C., preferably within the range of 15 to 37° C. Examples of the culture period can include a culture period within the range of 2 to 28 days, preferably within the range of 4 to 21 days, more preferably within the range of 5 to 14 days, even more preferably within the range of 6 to 10 days, still more preferably 7 days, from the viewpoint of the balance between more efficient manufacture of a vertebrate adipose tissue-derived mesenchymal cell line and manufacture in a shorter period. In the culture, the mature adipocyte, etc. may not be subcultured or may be subcultured.

In the step (B) described above, the vertebrate adipose tissue-derived mesenchymal cell line may be isolated from the medium after the ceiling culture, or may not be isolated. It is preferred to isolate the vertebrate adipose tissue-derived mesenchymal cell line therefrom. As the ceiling culture is continued, an established adipose tissue-derived mesenchymal cell line proliferates actively whereas the amount of the mature adipocyte decreases gradually. Therefore, a cell population rich in the adipose tissue-derived mesenchymal cell line can be obtained. For example, as the ceiling culture is continued for approximately 14 days, a cell population very rich in the adipose tissue-derived mesenchymal cell line can be obtained.

The ceiling culture performed in the step (B) described above also includes, for the sake of convenience, the continuation of culture by placing the culture container such that, after the adhesion of the mature adipocyte (easy-to-dedifferentiate mature adipocyte) obtained in the step (A) to the ceiling surface of the culture container, the adhesion surface is positioned at the bottom side of the culture container. The culture may be continued in the state where the mature adipocyte (easy-to-dedifferentiate mature adipocyte) obtained in the step (A) adheres to the ceiling surface of the culture container, to obtain an adipose tissue-derived mesenchymal cell line without performing culture by placing the culture container such that the adhesion surface is positioned at the bottom side of the culture container.

(Step C)

In the step (C) described above, the method for "culturing the adipose tissue-derived mesenchymal cell line in a modified medium for induction of differentiation into megakaryocytic cells containing an iron ion and an iron transporter, and collecting a platelet-like cell population from the culture product" is as described in the "method for manufacturing the platelet-like cell population of the present invention" mentioned above.

In the step (C) described above, the modified medium for induction of differentiation into megakaryocytic cells is free from bovine serum albumin, LDL cholesterol, deoxyribonucleotide triphosphate, and 2-mercaptoethanol and contains human serum albumin, iron-bound transferrin, insulin, and monothioglycerol. As a result, a much better platelet-like cell population having, for example, higher safety when applied to a human can be obtained. Preferred examples of the modified medium for induction of differentiation into megakaryocytic cells can include a modified MKLI medium of Example 2 mentioned later, and a medium containing each component having a concentration at a proportion within the range of 70 to 130% by weight (preferably within the range of 80 to 120% by weight) of each component independently with respect to the concentration of each component in the modified MKLI medium.

Hereinafter, the present invention will be described in detail with reference to Examples. However, the present invention is not limited by these Examples.

Example 1

[Creation of Adipose Tissue-Derived Mesenchymal Cell Line]

After isolation of a subcutaneous adipose tissue section from a human, collagenase (collagenase type II; manufactured by Sigma-Aldrich Co., LLC) was added thereto, and the mixture was incubated at 37° C. for 1 hour to obtain a cell suspension. As a result of centrifuging the cell suspension, mature adipocytes having a small specific gravity floated in a supernatant, and the other types of cells were precipitated as cell pellets. The cell pellets contained mesenchymal stem cells, preadipocytes, stromal cells (stroma cells), vascular endothelial cells, smooth muscle cells, fibroblasts, and the like. In subsequent experiments, cells of the cell pellets were used. The cells of the cell pellets mentioned above were cultured at 37° C. for 10 days under conditions involving a $CO_2$ concentration of 5% in a medium Adipocyte Differentiation Medium (manufactured by Cell Applications, Inc.) contained in a culture dish. The cells thus cultured were rich in mature adipocytes (easy-to-dedifferentiate mature adipocytes) differentiation-induced from a stromal vascular fraction including mesenchymal stem cells, preadipocytes, and stromal cells. The cultured cells were detached from the culture dish using trypsin. To the cells, trypsin and DMEM (Dulbecco's Modified Eagle's Medium, manufactured by Life Technologies Corp.) medium were added, and the mixture was applied to a centrifuge to collect mature adipocytes (easy-to-dedifferentiate mature adipocytes) floating in the supernatant. The easy-to-dedifferentiate mature adipocytes mentioned above were added to a culture flask containing a sufficient amount of DMEM medium containing 20% FBS. The cells were cultured while floating in and attaching to the upper inner surface of the culture flask filled with the medium (so-called "ceiling culture"). The ceiling culture was performed at 37° C. for 7 days under conditions involving a $CO_2$ concentration of 5%. The culture thus performed yielded a human adipose tissue-derived mesenchymal cell line. The conventional method (Japanese Patent No. 5055611) requires a period of a little over 2 months from the collection of an adipose tissue to the creation of a preadipocyte line. By contrast, this method of the present invention was able to create a large amount of an adipose tissue-derived mesenchymal cell line in less than 1 month from the collection of an adipose tissue. The obtained human adipose tissue-derived mesenchymal cell line was successively cultured in DMEM medium containing FBS (basal medium for preadipocyte culture).

In the case of creating a preadipocyte line from subcutaneous adipose tissue sections having the same size (1 cm square), the amount (cell count) of the cell line obtained per the same creation period (e.g., 2 months) was compared between the method of the present invention (method of creating easy-to-dedifferentiate mature adipocytes and then performing the ceiling culture of the cells to establish a cell line) and the conventional method (method of performing the ceiling culture of mature adipocytes collected from an adipose tissue to establish a cell line (Japanese Patent No. 5055611)). As a result, the method of the present invention yielded a cell line at approximately 15 times the cell count of the conventional method. This indicates that the method for manufacturing (establishing) a vertebrate adipose tissue-derived mesenchymal cell line according to the present invention can remarkably efficiently manufacture a mesenchymal cell line from a vertebrate adipose tissue. The obtained human adipose tissue-derived mesenchymal cell line maintained the ability to proliferate even at the 20th passage. Furthermore, the doubling time was observed to be 23 hours.

In Example 1, the human subcutaneous adipose tissue was used. The present inventors confirmed that use of a mouse subcutaneous adipose tissue yields an adipose tissue-derived mesenchymal cell line in the same way as above. The concentration of any culture medium component described in Examples below represents a final concentration in the culture medium.

Example 2

[Creation of Platelet-Like Cell Population of Present Invention from Adipose Tissue-Derived Mesenchymal Cell Line]

A medium was added to a culture dish. The medium used was a medium ("modified MKLI medium") reformed by the present inventors from MKLI (megakaryocyte lineage induction medium) medium known as a medium capable of inducing the differentiation of hematopoietic stem cells into megakaryocytes or platelet. The modified MKLI medium was created by adding 2 mM L-glutamine (manufactured by Life Technologies Corp.), 100 U/mL penicillin-streptomycin solution (manufactured by Life Technologies Corp.), 0.5% human serum albumin (manufactured by Sigma-Aldrich Co., LLC), 200 µg/mL iron-saturated transferrin (manufactured by Sigma-Aldrich Co., LLC), 10 µg/mL insulin (manufactured by Sigma-Aldrich Co., LLC), and 20 µM monothioglycerol (manufactured by Wako Pure Chemical Industries, Ltd.) to IMDM medium (Iscove's Modified Dulbecco's Medium, manufactured by Life Technologies Corp.) medium. The modified MKLI medium differs from the conventional MKLI medium in using human serum albumin instead of BSA, in not using LDL cholesterol, in not using dNTP, and in using monothioglycerol instead of mercaptoethanol.

The human adipose tissue-derived mesenchymal cell line created in Example 1 described above was cultured at 37° C. for 12 days under conditions involving a $CO_2$ concentration of 5% in the modified MKLI medium to obtain a cell population. Cells in the cell population were platelet-like cells that had a size of 1 to 10 µm, had no nucleus, and were similar to platelet. Therefore, the cell population was designated as a platelet-like cell population. The platelet-like cell population is also referred to as ASCL-PLC (platelet-like cells from adipose-derived mesenchymal stem/stromal cell line).

Example 3

[Analysis of Cell Surface Marker of Platelet-Like Cell Population—1]

The human adipose tissue-derived mesenchymal stem cell line created in Example 1 was processed by the induction of differentiation into megakaryocytic cells by the method described in Example 2. The platelet-like cell population (ASCL-PLC) was collected on 12 days after the differentiation induction and suspended in a PBS solution, followed by antigen-antibody reaction at 25° C. for 45 minutes in the presence of antibodies (see Table 1) labeled with a labeling material against 25 types of cell surface markers (CD9, CD10, CD13, CD26, CD29, CD36, CD41/CD61, CD42b, CD44, CD49b, CD61, CD63, CD72, CD73, CD77, CD81, CD90, CD95, CD107a, CD107b, CD140b, CD147, and CD164). Then, cells positive to the 25 types of cell surface markers were analyzed using a flow cytometer (FACSVerse [manufactured by BD Biosciences]) (see Table 2). For a control, the same processing as in ASCL-PLC was performed using platelet collected from peripheral blood of two healthy individuals, and cells positive to the 23 types of cell surface markers were analyzed.

TABLE 1

| Cell surface marker | Antibody |
| --- | --- |
| CD9 | Human Cell Surface Marker Screening Panel (manufactured by BD Biosciences) |
| CD10 | Human Cell Surface Marker Screening Panel (manufactured by BD Biosciences) |
| CD13 | Human Cell Surface Marker Screening Panel (manufactured by BD Biosciences) |
| CD26 | Human Cell Surface Marker Screening Panel (manufactured by BD Biosciences) |
| CD29 | Human Cell Surface Marker Screening Panel (manufactured by BD Biosciences) |
| CD36 | Human Cell Surface Marker Screening Panel (manufactured by BD Biosciences) |
| CD41/CD61 | anti-human CD41 (manufactured by BioLegend, Inc.), or, Human Cell Surface Marker Screening Panel (manufactured by BD Biosciences) |
| CD42b | anti-human CD42b (manufactured by BioLegend, Inc.), or, Human Cell Surface Marker Screening Panel (manufactured by BD Biosciences) |
| CD44 | Human Cell Surface Marker Screening Panel (manufactured by BD Biosciences) |
| CD49b | Human Cell Surface Marker Screening Panel (manufactured by BD Biosciences) |
| CD61 | Human Cell Surface Marker Screening Panel (manufactured by BD Biosciences) |
| CD63 | Human Cell Surface Marker Screening Panel (manufactured by BD Biosciences) |
| CD72 | Human Cell Surface Marker Screening Panel (manufactured by BD Biosciences) |
| CD73 | Human Cell Surface Marker Screening Panel (manufactured by BD Biosciences) |
| CD77 | Human Cell Surface Marker Screening Panel (manufactured by BD Biosciences) |
| CD81 | Human Cell Surface Marker Screening Panel (manufactured by BD Biosciences) |
| CD90 | anti-human CD90 (manufactured by BioLegend, Inc.), or, Human Cell Surface Marker Screening Panel (manufactured by BD Biosciences) |
| CD95 | Human Cell Surface Marker Screening Panel (manufactured by BD Biosciences) |
| CD107a | Human Cell Surface Marker Screening Panel (manufactured by BD Biosciences) |
| CD107b | Human Cell Surface Marker Screening Panel (manufactured by BD Biosciences) |
| CD140b | Human Cell Surface Marker Screening Panel (manufactured by BD Biosciences) |
| CD147 | Human Cell Surface Marker Screening Panel (manufactured by BD Biosciences) |
| CD164 | Human Cell Surface Marker Screening Panel (manufactured by BD Biosciences) |

TABLE 2

| Cell surface marker | ASCL-PLC | Human platelet-1 | Human platelet-2 |
| --- | --- | --- | --- |
| CD9 | 6.1 | 81.9 | 82.3 |
| CD10 | 8.8 | 1.2 | 0.7 |
| CD13 | 45.9 | 0.7 | 0.2 |
| CD26 | 25.9 | 2.5 | — |
| CD29 | 80.2 | 99.5 | 99.8 |
| CD36 | 3.6 | 86.4 | 99.5 |
| CD41/CD61 | 3.8 | 98.4 | 98.8 |
| CD42b | 13.6 | 98.4 | 98.9 |
| CD44 | 47.3 | 2.5 | 0.6 |
| CD49b | 44.9 | 92.1 | 99.2 |
| CD61 | 1.2 | 98.9 | 98.6 |
| CD63 | 69.4 | 52.6 | 32.3 |
| CD72 | 2.4 | 0.7 | — |

TABLE 2-continued

| Cell surface marker | ASCL-PLC | Human platelet-1 | Human platelet-2 |
| --- | --- | --- | --- |
| CD73 | 63.0 | 0.2 | 0.3 |
| CD77 | 11.3 | 5.7 | — |
| CD81 | 13.9 | 3.7 | — |
| CD90 | 52.0 | 1.1 | 0.7 |
| CD95 | 31.0 | 4.1 | — |
| CD107a | 56.5 | 29.8 | 16.3 |
| CD107b | 33.5 | 1.8 | 2.0 |
| CD140b | 6.2 | 6.9 | 4.2 |
| CD147 | 15.3 | 97.7 | 93.2 |
| CD164 | 24.3 | 4.2 | 3.6 |

The numeric values in the table represent the proportion (%) of cells expressing each cell surface marker as to 3 types of cells (ASCL-PLC, human platelet-1, and human platelet-2). The mark "−" in the table represents being less than the detection limit (0.1%).

In the platelet, the proportions of cells expressing the platelet surface markers (e.g., CD9, CD29, CD36, CD41/61, CD42b, CD49b, CD61, and CD147) were high (see Table 2). On the other hand, referring to the platelet surface markers in ASCL-PLC, the proportion of cells expressing CD63 was higher than that in the platelet. The proportion of cells expressing CD29 was slightly lower than that in the platelet. The proportions of cells expressing CD9, CD36, CD41/61, CD42b, CD61, and CD147 were much lower than those in the platelet.

Also referring to the mesenchymal cell surface markers (e.g., CD90, CD13, CD26, CD44, CD73, CD77, CD81, CD95 and CD164), the proportions of cells expressing these mesenchymal cell surface markers in ASCL-PLC were much higher than those in the platelet (see Table 2).

These results indicate that ASCL-PLC is a cell population comprising platelet-like cells expressing one or more platelet surface markers and platelet-like cells expressing one or more mesenchymal cell surface markers. Results of costaining CD42b and CD90 (FIG. 1) indicate that ASCL-PLC comprises platelet-like cells coexpressing the platelet surface marker CD42b and the mesenchymal cell surface marker CD90 (i.e., platelet-like cells positive to CD42b and positive to CD90). Thus, ASCL-PLC was shown to be a cell population comprising cells coexpressing surface antigens of different cell differentiation lineages, i.e., blood cells and mesenchymal cells.

Example 4

[Analysis of Cell Surface Marker of Platelet-Like Cell Population—2]

Cell surface markers of the platelet-like cell population were analyzed by the same method as described in Example 3 except that the cell surface markers to be analyzed were set to CD41 and CD42b. The analysis of the cell surface markers was conducted on 4 days, 6 days, 8 days, 10 days, 12 days and 14 days after induction of differentiation into megakaryocytic cells. The antibody against CD41 used was anti-human CD41 (manufactured by BioLegend, Inc.). The antibody against CD42b used was anti-human CD42b (manufactured by BioLegend, Inc.).

Results of costaining CD41 and CD42b are shown in FIG. 2. As is evident from the results of FIG. 2, cells expressing platelet-specific surface antigens were observed with the number of culture days when the mesenchymal cell line was cultured using a modified medium for induction of differentiation into megakaryocytic cells.

Example 5

[Analysis of Wound Healing Effect Brought About by ASCL-PLC]

A complete loss of 8 mm in diameter was formed in each NSG mouse (manufactured by Oriental Yeast Co., Ltd.), which is an immunodeficient mouse. A single dose of PBS, human platelet, ASCL-PLC ($4 \times 10^7$ cells which were the same number of the human platelet), or human basic fibroblast growth factor (bFGF) was topically applied to each wound. The rate of wound area reduction was analyzed over time (see FIGS. 3A and 3B).

As a result, the treatment of the wound site using ASCL-PLC exhibited a high wound area reducing effect as compared with use of the platelet (see day 7 in FIGS. 3A and 3B). As a result of pathologically analyzing tissue samples, use of ASCL-PLC was confirmed to form a granulation tissue and ameliorate a layered construction at a relatively early stage (on at least 5 days after the topically application), also because of the high adhesion efficiency of ASCL-PLC to the wound site (see FIG. 3C). On the other hand, such an effect was not observed in the case of using platelet.

The results described above indicate that ASCL-PLC has a higher wound healing effect than that of platelet generally used in the clinical practice of wound treatment.

Example 6

[Cytokine Producing Effect of ASCL-PLC]

ASCL-PLC and human platelet were each suspended at $20 \times 10^8$ cells/mL in 20 μL of phosphate-buffered saline (PBS solution) and stimulated with 10 mM $CaCl_2$ for 15 minutes, followed by the measurement of the amounts of various cytokines produced in the PBS solution using an ELISA kit (FGF basic Human ELISA Kit, manufactured by Abcam plc). Preferred examples of the formulation of the PBS solution used in the suspension described above include 8 g/L NaCl, 0.2 g/L KCl, 1.44 g/L $Na_2HPO_4$, and 0.24 g/L $KH_2PO_4$ (pH 7.4).

As a result, the cells of both ASCL-PLC and human platelet were confirmed to release cytokines (bFGF, PDGF, VEGF-A, TGF-β, and EGF) considered to be important for wound healing (see FIG. 4). However, the amount of bFGF (basic fibroblast growth factor), an existing wound healing drug, produced was remarkably higher in ASCL-PLC than in human platelet and was approximately 60 times that in the human platelet (see FIG. 4A).

INDUSTRIAL APPLICABILITY

The present invention can provide, for example, a more practical wound healing accelerator that more effectively accelerates wound healing. More specifically, the present invention can provide, for example, a more practical wound healing accelerator that is easily obtained in a larger amount than that of peripheral blood platelet and has a better wound healing effect than that of peripheral blood platelet.

The invention claimed is:

1. A method for accelerating wound healing, the method comprising manufacturing platelets that co-express one or more platelet surface markers and one or more mesenchymal cell surface markers and topically administering the platelets thus manufactured to a patient in need of wound healing, wherein manufacturing the platelets comprises:

(A) inducing differentiation of one or more cells into mature adipocytes, the one or more cells having been selected from a stromal vascular fraction comprising a mesenchymal stem cell, a preadipocyte, and a stromal cell of vertebrate adipose tissue;

(B) inducing a dedifferentiation of the mature adipocyte obtained in step (A) to obtain a vertebrate adipose tissue-derived mesenchymal cell line;

(C) culturing the adipose tissue-derived mesenchymal cell line obtained in step (B) in a medium for induction of differentiation into megakaryocytic cells containing an iron ion and an iron transporter, and collecting platelets from the culture product; and (D) stimulating the platelets obtained in step (C) with calcium.

2. The method according to claim 1, wherein manufacturing the platelets comprises manufacturing platelets in which the proportion of CD29-positive platelets is 60% or more, the proportion of CD42b-positive platelets is 5% or more, and the proportion of CD90-positive platelets is 30% or more.

3. The method according to claim 1, wherein manufacturing the platelets comprises manufacturing a population of platelets that satisfies one or more of the following conditions: the proportion of CD9-positive cells is 30% or less; the proportion of CD13-positive cells is 30% or more; the proportion of CD26-positive cells is 15% or more; the proportion of CD36-positive cells is 40% or less; the proportion of CD41/61-positive cells is 60% or less; the proportion of CD42b-positive cells is 5% or more; the proportion of CD41-positive cells is 20% or more; the proportion of CD44-positive cells is 30% or more; the proportion of CD49b-positive cells is 30% or more; the proportion of CD61-positive cells is 30% or less; the proportion of CD63-positive cells is 60% or more; the proportion of CD73-positive cells is 40% or more; the proportion of CD95-positive cells is 20% or more; the proportion of CD107b-positive cells is 20% or more; the proportion of CD147-positive cells is 50% or less; and the proportion of CD164-positive cells is 15% or more.

4. The method according to claim 1, wherein the one or more cells.

5. The method according to claim 1, wherein an amount of a basic fibroblast growth factor produced by the platelets is 10 or more times an amount of the basic fibroblast growth factor produced by a population of peripheral platelets of control when platelets and peripheral platelets of control are suspended at $20 \times 10^8$ cells/mL in 20 µL of phosphate-buffered saline and stimulated with 10 mM $CaCl_2$ for 15 minutes, and then the amount of the basic fibroblast growth factor in the phosphate-buffered saline is measured.

6. The method according to claim 1, wherein the wound is one or more wounds selected from the group consisting of incised wound, lacerated wound, chop wound, puncture wound, impalement wound, contused wound, dermabrasion, bite wound, gunshot wound, pressure ulcer, cut, rupture, sting, bruising, bite, abrasion, burn, erosion, surgical wound, and anastomotic leakage.

7. The method according to claim 1, wherein manufacturing comprises selecting the medium for induction of differentiation into megakaryocytic cells in step (C) to be the modified medium for induction of differentiation into megakaryocytic cells in step (C) and wherein the modified medium for induction of differentiation into megakaryocytic cells in step (C) is free from bovine serum albumin, LDL cholesterol, deoxyribonucleotide triphosphate, and 2-mercaptoethanol and contains human serum albumin, iron-bound transferrin, insulin, and monothioglycerol.

8. The method according to claim 7, wherein after obtaining the adipose tissue-derived mesenchymal cell line in step (B) and before culturing the cell line in the modified medium for induction of differentiation into megakaryocytic cells containing an iron ion and an iron transporter in step (C), a selection of a cell by using the presence or absence of an expression of a particular cell surface marker as an index is not performed for the cell line.

9. The method according to claim 1, wherein in step (C), the method for collecting the platelets from the culture product does not comprise a selection of a platelet by using the presence or absence of an expression of a particular cell surface marker as an index.

10. The method according to claim 2, wherein the platelet-like cell population further satisfies one or more of the following conditions: the proportion of CD9-positive cells is 30% or less; the proportion of CD13-positive cells is 30% or more; the proportion of CD26-positive cells is 15% or more; the proportion of CD36-positive cells is 40% or less; the proportion of CD41/61-positive cells is 60% or less; the proportion of CD42b-positive cells is 5% or more; the proportion of CD41-positive cells is 20% or more; the proportion of CD44-positive cells is 30% or more; the proportion of CD49b-positive cells is 30% or more; the proportion of CD61-positive cells is 30% or less; the proportion of CD63-positive cells is 60% or more; the proportion of CD73-positive cells is 40% or more; the proportion of CD95-positive cells is 20% or more; the proportion of CD107b-positive cells is 20% or more; the proportion of CD147-positive cells is 50% or less; and the proportion of CD164-positive cells is 15% or more.

11. The method according to claim 2, wherein the platelets are human-derived platelets.

12. The method according to claim 3, wherein the platelets are human-derived platelets.

13. The method according to claim 1, wherein the platelets further satisfy the following condition:
the proportion of CD107a-positive platelets is 15% or more.

14. The method according to claim 1, wherein the wound is a skin ulcer.

* * * * *

UNITED STATES PATENT AND TRADEMARK OFFICE
CERTIFICATE OF CORRECTION

| | |
|---|---|
| PATENT NO. | : 11,712,451 B2 |
| APPLICATION NO. | : 16/162546 |
| DATED | : August 1, 2023 |
| INVENTOR(S) | : Yumiko Matsubara et al. |

It is certified that error appears in the above-identified patent and that said Letters Patent is hereby corrected as shown below:

In the Claims

Replace, "4. The method according to claim 1, wherein the one or more cells." with, "4. The method according to claim 1, wherein the one or more cells are human-derived."

Signed and Sealed this
Seventh Day of November, 2023

Katherine Kelly Vidal
*Director of the United States Patent and Trademark Office*